United States Patent

Kamata et al.

Patent Number: 5,319,099
Date of Patent: Jun. 7, 1994

[54] 3-BENZYLIDENE-1-CARBAMOYL-2-PYR-ROLIDONE COMPOUNDS USEFUL AS ANTIINFLAMMATORY AGENTS

[75] Inventors: Susumu Kamata, Hyogo; Takeshi Shiota, Kyoto; Nobuhiro Haga, Osaka; Toshihiko Okada; Hirokuni Jyoyama, both of Nara; Saichi Matsumoto, Osaka, all of Japan

[73] Assignee: Shionogi Seiyaku Kabushiki Kaisha, Osaka, Japan

[21] Appl. No.: 862,761

[22] PCT Filed: Jan. 14, 1992

[86] PCT No.: PCT/JP92/00020

§ 371 Date: Jun. 24, 1992

§ 102(e) Date: Jun. 24, 1992

[87] PCT Pub. No.: WO92/12966

PCT Pub. Date: Aug. 6, 1992

[30] Foreign Application Priority Data

Jan. 21, 1991 [JP] Japan .................. 3-021618

[51] Int. Cl.$^5$ .............. C07D 207/24; C07D 231/02; C07D 263/02; C07D 277/02; A61K 31/40; A61K 31/41

[52] U.S. Cl. .................. 548/538; 544/141; 548/188; 548/225; 548/243; 548/323.1; 548/369.7; 548/111

[58] Field of Search .............. 548/538, 323.1, 369.7, 548/141, 188, 225, 243

[56] References Cited

U.S. PATENT DOCUMENTS

| | | | |
|---|---|---|---|
| 3,485,632 | 12/1969 | Ohlschlager et al. | 548/369.7 |
| 3,624,081 | 11/1971 | Dickinson et al. | 548/538 X |
| 3,686,204 | 8/1972 | Munz et al. | 548/323.1 |
| 4,153,713 | 5/1979 | Huth et al. | 548/538 |
| 4,861,794 | 8/1989 | Otterness | 514/414 |
| 5,191,084 | 3/1993 | Bagli et al. | 546/279 |

FOREIGN PATENT DOCUMENTS

| | | | |
|---|---|---|---|
| 58-079944 | 5/1983 | Japan | 548/323.1 |
| 61-218571 | 3/1985 | Japan | 548/538 |
| 61-257967 | 5/1985 | Japan | 548/538 |
| 62-029570 | 7/1985 | Japan | 548/323.1 |
| 62-042977 | 2/1987 | Japan | 548/323.1 |

Primary Examiner—Floyd D. Higel
Attorney, Agent, or Firm—Wenderoth, Lind & Ponack

[57] ABSTRACT

The present invention relates to novel 3-benzylidene-1-carbamoyl-2-pyrroridone analogues having advantage anti-inflammatory activities, which is represented by the formula:

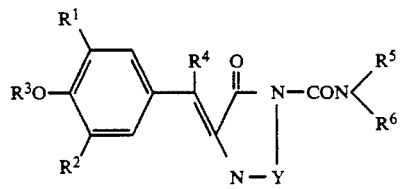

wherein $R^1$ and $R^2$ each is independently hydrogen, alkyl, alkoxy, or halogen; $R^3$ is hydrogen or acyl; $R^4$ is hydrogen, alkyl, hydroxy, alkoxy, cyano, or halogen; $R^5$ and $R^6$ each is independently hydrogen, alkyl, aryl, aralkyl, heterocyclic group, substituted or unsubstituted amino, or $OR^7$ wherein $R^7$ is hydrogen, alkyl, aryl, acyl, or aralkyl, or taken together with the adjacent nitrogen atom may form heterocyclic group which may contain N, O, and/or S, and X and Y each is independently O, S, substituted or unsubstituted imino, or substituted or unsubstituted methylene. In more detail, the present invention provides an anti-inflammatory agent which is useful for the treatment of chronic inflammation and has little side effect, e.g., stomach disease.

11 Claims, No Drawings

3-BENZYLIDENE-1-CARBAMOYL-2-PYRROLIDONE COMPOUNDS USEFUL AS ANTIINFLAMMATORY AGENTS

FIELD OF THE INVENTION

The present invention relates to novel 3-benzylidene-1-carbamoyl-2-pyrrolidone analogues which have inhibitory activities against the production of leukotriene $B_4$ ($LTB_4$) and that of interleukin-1 (IL-1). In more detail, these derivatives are able to be applied to safe medicaments which show potent anti-inflammatory effects to acute and chronic inflammation and hardly cause stomach disease.

BACKGROUND OF THE INVENTION

Prior anti-inflammatory agents of non-steroid type are effective to the improvement in the early stages of rheumatism and acute inflammation, however, have some defects of being no effective to progressed rheumatic diseases such as osteonecrosis, the improvement in chronic rheumatic diseases, or the treatment of arthrosteitis etc., and of having potent activities to induce gastric ulcer caused by the inhibition of the production of prostaglandin $E_2$ ($PGE_2$).

Recently it has been revealed that leukotriene (LT), esp. $LTB_4$ etc., which is a metabolite produced via the metabolism of arachidonic acid caused by 5-lipoxygenase, is an important mediator in inflammation reaction. Furthermore, it has been suggested that the cause of inflammation relates to IL-1 which is a kind of cytokines and that also chronic rheumatism is much influenced by cytokines such as IL-1.

In view of circumstances above, attentions have been paid to compounds having inhibitory activities against the production of $LTB_4$ and IL-1, as a new type of anti-inflammatory agent. These compounds are much useful than known non-steroidal anti-inflammatories, in respect of that they are expected to have efficacy not only to acute inflammation but also to chronic inflammation, e.g., chronic arthrorheumatism etc.

With an intention to develop such anti-inflammatory agents as described above, a wide variety of compounds are disclosed in specifications of Kokai 58-79944, Kokai 61-257967, Kokai 62-42977, Kokai 1-305028, Kokai 2-4729, Kokai 2-256645, Kokai 2-270865, and Kokai 1-503782.

As stated above, it has been desired to develop anti-inflammatory agents capable of inhibiting the production of mediators relating to inflammation such as $PGE_2$, $LTB_4$, and IL-1, however, such an anti-inflammatory agent as being useful for treating chronic inflammation and having little side effect, e.g., stomach disease, has not been developed yet.

DISCLOSURE OF THE INVENTION

The present inventors have tried to find that the compounds of the formula (I):

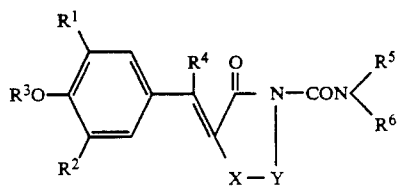

(I)

wherein $R^1$ and $R^2$ each is independently hydrogen, alkyl, alkoxy, or halogen; $R^3$ is hydrogen or acyl; $R^4$ is hydrogen, alkyl, hydroxy, alkoxy, cyano, or halogen; $R^5$ and $R^6$ each is independently hydrogen, alkyl, aryl, aralkyl, heterocyclic group, substituted or unsubstituted amino, or $OR^7$ wherein $R^7$ is hydrogen, alkyl, aryl, acyl, or aralkyl, or taken together with the adjacent nitrogen atom may form heterocyclic group which may contain N, O, and/or S, and X and Y each is independently O, S, substituted or unsubstituted imino, or substituted or unsubstituted methylene, give advantageous anti-inflammatory activities applicable to an agent for treating chronic inflammation, and that side effects thereof, e.g., stomach disease, are extremely weaker than prior anti-inflammatory agents, whereby they have completed the present invention. The present invention is characterized by its potent inhibitory activities against the production of IL-1.

In the present specification, "alkyl" means straight or branched $C_1$–$C_{10}$ alkyl, and preferred is straight or branched $C_1$–$C_6$ alkyl, including, for example, methyl, ethyl, n-propyl, i-propyl, n-butyl, i-butyl, s-butyl, t-butyl, n-pentyl, i-pentyl, neopentyl, s-pentyl, t-pentyl, n-hexyl, neohexyl, i-hexyl, s-hexyl, t-hexyl, and the like.

As alkyl meant in the definition for $R^1$ and $R^2$, most preferred is branched $C_3$ or $C_4$ alkyl, i.e., i-propyl or t-butyl. As alkyl meant in the definition for $R^4$, especially preferred is $C_1$ or $C_2$ alkyl, i.e., methyl or ethyl. As alkyl meant in the definition for $R^5$ and $R^6$, especially preferred is straight or branched $C_1$–$C_3$ alkyl, e.g., methyl, ethyl, n-propyl, and i-propyl.

"Alkoxy" means the group derived from "alkyl" defined above, and preferred is $C_1$ or $C_2$ alkoxy, i.e., methoxy or ethoxy.

"Halogen" means fluorine, chlorine, bromine, and iodine.

"Acyl" means aromatic or aliphatic acyl. Aromatic acyl includes, for example, benzoyl, 4-hydroxybenzoyl, 4-chlorobenzoyl, 4-methoxybenzoyl, 4-nitrobenzoyl, 4-tert-butylbenzoyl, benzenesulfonyl, toluenesulfonyl etc. Aliphatic acyl includes, for example, formyl, acetyl, propionyl, butyryl, and valeryl. Preferred is aliphatic acyl, esp. acetyl.

"Heterocyclic group" meant in the definition for $R^5$ and $R^6$ means 5 to 6 membered heterocyclic group containing, one or more hetero atoms selected from the group consisting of oxygen, sulfur, and nitrogen as ring-forming atom, and which includes for example, pyrrolyl, imidazolyl, pyrazolyl, pyridyl, pyridazinyl, pyrimidinyl, pyrazinyl, 1,3,5-triazinyl, 1,2,4-triazinyl, 1,2,3-triazinyl, isoxazolyl, oxazolyl, 1,2,3-oxadiazolyl, 1,2,4-oxadiazolyl, 1,2,5-oxadiazolyl, 1,3,4-oxadiazolyl, isothiazolyl, thiazolyl, 1,2,3-thiadiazolyl, 1,2,4-thiadiazolyl, 1,2,5-thiadiazolyl, 1,3,4-thiadiazolyl, tetrazolyl, furyl, thienyl, pyrrolidinyl, piperidyl, morpholinyl, thiomorpholinyl, piperazinyl, pyranyl, and thiopyranyl, etc, and most preferred is morpholinyl or thiomorpholinyl.

"Heterocyclic group" formed by $R^5$ and $R^6$ taken together means 5 to 6 membered heterocyclic group which may further contain, one or more hetero atoms selected from the group consisting of oxygen, sulfur, and nitrogen as ring-forming atom except for the nitrogen, including, for example, pyrrolyl, imidazolyl, pyrazolyl, 1,3,5-triazinyl, 1,2,4-triazinyl, 1,2,3-triazinyl, pyrrolidinyl, piperidyl, or morpholinyl, and thiomorpholinyl etc., and most preferred is morpholinyl or thiomorpholinyl.

The substituent group meant in the term "substituted or unsubstituted amino" includes alkyl, hydroxy, alkoxy, acyl, and alkoxycarbonyl, where the said alkyl, alkoxy, and acyl have the same meaning as those described above, and preferred is methyl, ethyl, methoxy, ethoxy, acetyl, or benzoyl. Alkoxycarbonyl includes, for example, methoxycarbonyl, ethoxycarbonyl, tert-butoxycarbonyl, and benzyloxycarbonyl, and most preferred is tert-butoxycarbonyl.

"Aralkyl" means a group of alkyl described above which is substituted by aryl at any position, with a proviso that aryl means $C_6$-$C_{12}$ aromatic ring, including, for example, phenyl, tolyl, xylyl, biphenyl, and naphthyl etc. The aralkyl includes, for example, benzyl, phenethyl, and phenylpropyl etc., and most preferred is benzyl.

The substituent meant in the term "imino which is substituted or not" includes alkyl and alkoxy described above, and preferred is methyl, ethyl, methoxy, or ethoxy.

The substituent meant in the term "methylene which is substituted or not" includes alkyl, alkoxy, hydroxy, and halogen each of which is described above. The said alkyl may be substituted at its terminal carbon by hydroxy or substituted or unsubstituted carboxy, with a proviso that the substituted carboxy means esterified carboxy or carboxy substituted by alkali metal or alkaline earth metal. Esterified carboxy means one described above, and preferred is methoxycarbonyl or ethoxycarbonyl. Alkali metal means lithium, sodium, potassium, rubidium, and cesium. Alkaline earth metal means beryllium, magnesium, calcium, and strontium. Preferred is sodium, potassium, or calcium.

The present invention includes two kinds of isomers which are differentiable by the formation of its double bond, i.e., E-isomer or Z-isomer, or the mixture thereof.

The representative production methods of the compounds (I) of the present invention are shown below.

PRODUCTION METHOD 1

The compounds (I) of the present invention are prepared by reacting the compound of the formula (II):

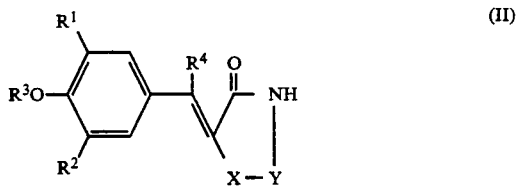
(II)

wherein $R^1$, $R^2$, $R^3$, $R^4$, X, and Y are the same as defined above, with a carbamoyl reagent of the compound (III):

$R^8$—CO—$NR^{5'}R^{6'}$ (III)

wherein $R^{5'}$ and $R^{6'}$ each is independently hydrogen, alkyl, heterocyclic group substituted or unsubstituted amino which may be protected, $OR^{7'}$ (wherein $R^{7'}$ is hydrogen, alkyl, acyl, or aralkyl, each of which may be protected), or taken together with the adjacent nitrogen atom may form heterocyclic group which may contain N, O, and/or S; $R^8$ is releasing group, if necessary, followed by subjecting to deprotection reaction.

It is preferable to carry out the present reaction under basic conditions. In the case that such a base is sodium ethoxide, sodium tert-butoxide, sodium hydride, sodium amide, lithium diisopropylamide, lithium bis(trimethylsilyl)amide, or n-butyllithium etc., the reaction is able to be carried out at room temperature in an aprotic polar solvent including, for example, tetrahydrofuran, dimethylformamide, dimethylacetamide, dimethyl sulfoxide, N-methylpyrrolidone, and hexamethylphosphoramide, etc. In the case that such a base is amines including, for example, pyridine, triethylamine etc., it is preferable to carry out the reaction under heating, if necessary, in the inert solvents including, for example, aromatic hydrocarbons (e.g., toluene, benzene, and chlorobenzene etc.), chlorinated hydrocarbons (e.g., chloroform and dichloromethane etc.), ketones (acetone), and ethers (tetrahydrofran).

The amino protecting group meant in the definition for $R^{5'}$ and $R^{6'}$ means that usually used as amino protecting group, which includes, for example, trifluoroacetyl, benzyloxycarbonyl, tert-butoxycarbonyl, and triphenylmethyl etc.

For the hydroxy-protecting group meant in the definition for $OR^{7'}$, any one stable under basic conditions can be used, which includes, for example, triethylsilyl, tert-butyldimethylsilyl, tert-butyldiphenylsilyl, tetrahydropyranyl, methoxymethyl, methylthiomethyl, 2-methoxyethoxymethyl, 1-ethoxyethyl, benzyl, and methoxybenzyl etc.

The elimination group in the definition for $R^8$ means phenyloxy which may be substituted by electron-withdrawing group, and which includes, for example, phenoxy, 4-nitrophenoxy, 4-nitrosophenoxy, 4-chlorophenoxy, 4-acetyphenoxy, and 4-trifluoromethylphenoxy etc.

Another production methods for some of the compounds (I) of the present invention are as follows:

that the compounds (I) wherein $R^5$ and $R^6$ are hydrogen at the same time can be prepared by adding isocyanate (e.g., chlorosulfonyl isocyanate, trichloroacetyl isocyanate, and tert-butyl isocyanate etc.) to the compound (II), followed by treating with acid, and that the compounds (I) wherein either $R^5$ or $R^6$ is not hydrogen can be prepared by adding isocyanate which is represented, by the formula: O=C=N—$R^{5'}$ (wherein $R^{5'}$ is the same as defined above) for example methyl isocyanate, ethyl isocyanate, and dimethyl-tert-butyl-silyloxyisocyanate etc., if necessary, followed by deprotection.

PRODUCTION METHOD 2

The compound (I) of the present invention are prepared by reacting the compound of the formula (IV):

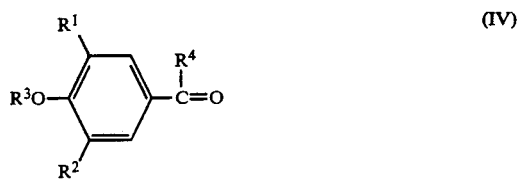
(IV)

wherein $R^1$, $R^2$, $R^3$, and $R^4$ each is the same as defined above, with Wittig reagent of the formula (V):

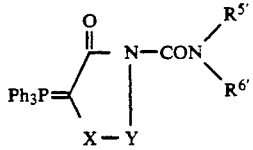

wherein Ph is phenyl; X, Y, R⁵′, and R⁶′ are the same as defined above, under the condition for Wittig reaction.

Wittig reagent (V) is prepared by reacting the compound of the formula (VI):

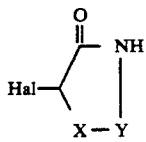

wherein Hal is halogen, X and Y each is the same as defined above, with Carbamoyl reagent (III) described above, to obtain the compound of the formula (VII):

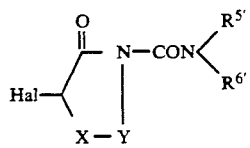

wherein Hal, X, Y, R⁵′, and R⁶′ each is the same as defined above, followed by treating, accoding to the usual methods, with triphenylphosphine and base.

Furthermore, the compounds (I) of the present invention are prepared also by condensing the compound (IV), under the condition for Reformatsky reaction, with organic zinc compound of the formula (VIII):

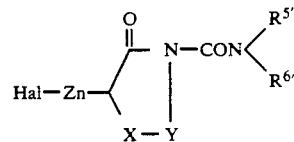

wherein Hal, X, Y, R⁵′, and R⁶′ each is the same as defined above, which is prepared by the reaction of the compound (VII) with metallic Zinc.

The compounds of the present invention are effective for hyperthermia, analgesic, cold disease, acute and chronic tracheitis, inflammation caused by trauma or operation, arthritis, rheumatism, neuralgia, arthralgia, metabolic osteopathy, and the like, because of having advantageous anti-inflammatory effects besides that its side-effects, e.g., stomach disease, are very weak. The compounds of the present invention are especially useful for treating diseases necessary to long-term administration which include, chronic rheumatoid arthritis, osteoarthritis, and osteoporosis.

The compounds (I) of the present invention may be formulated into the composition for typical use such as injection, oral, and anal administration etc., together with various kinds of carriers. Though the dosage is not regulated because it varies depending on the kind of disease, the degree of disease, the route of administration, the age and weight of a patient etc., it is usually in the range from 10 mg to 500 mg, preferably from 50 mg to 150 mg, per day for an adult.

The present invention is explained in more detail by the following Examples and Experiments, however, which will not limit the scope of the present invention.

EXAMPLE

EXAMPLE 1

(1) The Preparation of N-carbamoyl-3-bromopyrrolidin-2-one

A solution of 30 g of 2,4-dibromobutyryl chloride (J. Med. Chem., p1995, 30. 1987) and 13.63 g of urea dissolved into 150 ml of benzene was heated at 90° C. with stirring for 3 hours. The reaction mixture was cooled to room temperature, then a very excessive amount of ethyl acetate was added thereto. The layer of ethyl acetate was washed with an aqueous solution of sodium bicarbonate and saturated brine, then the resulting solution was dried over magnesium sulfate and evaporated. The obtained residue (28 g) was dissolved into 30 ml of tetrahydrofuran (THF) and cooled. To this mixture was added 4.7 g of NaH (55% in mineral oil) bit by bit, then the mixture was stirred at room temperature for 2 hours. The reaction mixture was evaporated to make the amount of the solution about 50 ml, then which was poured into ethyl acetate. The layer of ethyl acetate was washed with water and saturated brine, dried over magnesium sulfate, and evaporated. The obtained residue was washed well with n-hexane, whereby 15.7 g of the objective compound was obtained in 66% yield.

Mp. 127.5°–129° C.

IR(KBr)νmax cm⁻¹: 1726, 1700(CO).

NMR(CDCl₃) δ ppm: 2.19–2.41(1H,m), 2.52.–2.71(1H,m), 3.80–4.05(2H,m), 4.52–4.59(1H,m), 5.2–5.8(1H,m), 7.8–8.3(1H,m).

(2) The Preparation of N-carbamoyl-3-(3,5-di-tert-butyl-4-hydroxybenzylidene)pyrrolidin-2-one (Ia-1)

A solution of 2.0 g of N-carbamoyl-3-bromopyrrolidin-2-one (9.7 mmole) and 2.78 g of triphenylphosphine (10.6 mmole) in 30 ml of THF was stirred under heating at 70° C. for 20 hours. The reaction mixture was cooled down to room temperature, then the precipitated crystals were collected. The obtained Wittig salt (1.34 g, 2.86 mmole), 3,5-di-tert-butyl-4-hydroxybenzaldehyde (670 mg, 2.86 mmole), and triethylamine (580 mg, 5.73 mmole) were dissolved into 60 ml of ethanol, and the mixture was stirred under heating at 70° C. for 2 hours. The reaction mixture was evaporated, then the residue was dissolved into ethyl acetate, which was washed with water and saturated brine, dried over magnesium sulfate, and evaporated. The residue was separated by using silica gel chromatography (toluene:ethyl acetate=3:1) and recrystallized from dichloromethane-n-hexane, whereby 600 mg of the objective compound was obtained in 17.1% yield. The physical constants are described on Table 1.

EXAMPLE 2

The Preparation of N-(N-methylcarbamoyl)-3-(3,5-di-tert-butyl-4-hydroxybenzylidene)pyrrolidin-2-one (Ia-2)

Methyl isocyanate (5.0 ml) was added to 3-(3,5-di-tert-butyl-4-hydroxybenzylidene)pyrrolidin-2-one (277 mg, 0.75 mmole) (J. Med. Chem., p1995, 30, 1987) and the mixture was heated under reflux for 15 hours. The reaction mixture was evaporated under reduced pressure to obtain a residue, which was purified by using silica gel chromatography (n-hexane:ethyl acetate=4:1) and recrystallized from dichloromethane-ether, whereby 189 mg of the objective compound was obtained as white crystal in 70.3% yield. The physical constants are described on Table 1.

EXAMPLE 3

N-(N,N-dimethylcarbamoyl)-3-(3,5-di-tert-butyl-4-hydroxybenzylidene)pyrrolidin-2-one (Ia-3)

To a solution of 301 mg of 3-(3,5-di-tert-butyl-4-hydroxybenzylidene)pyrrolidine-2-one (1.0 mmole) dissolved into 5 ml of DMF, NaH (60% in mineral oil, 85 mg, 2.1 mmole) was added under ice-cooling. The resulting mixture was stirred at room temperature for 30 min, then the solution was cooled again. N,N-Dimethylphenylcarbamate (282 mg, 1.71 mmole) which was prepared according to the method described in J. Org. Chem., p660, 21, 1956, was added thereto, then the resulting solution was stirred at room temperature for 3 hours. The reaction mixture was poured into ethyl acetate, which was washed with 1N-HCl, water, and saturated brine, dried over magnesium sulfate, and evaporated. The obtained residue was separated by using silica gel chromatography (toluene:ethyl acetate=2:1) and recrystallized from ether-n-hexane, whereby 190 mg of the objective compound was obtained in 51% yield. The physical constants are described on Table 1.

EXAMPLE 4

N-(N-hydroxycarbamoyl)-3-(3,5-di-tert-butyl-4-hydroxybenzylidene)pyrrolidin-2-one (Ia-4)

3-(3,5-Di-tert-butyl-4-hydroxybenzylidene)pyrrolidine-2-one (301 mg, 1.0 mmole) and N-hydroxyphenylcarbamate-O-tert-butyldimethylsilylether (401 mg, 15 mmole) which was prepared according to the method described in J. Org. Chem., p660, 21, 1956, were dissolved into 5 ml of pyridine, and the solution was heated under reflux for 3 hours. The reaction mixture was poured into ethyl acetate, which was washed with 0.1N—HCl, water, and saturated brine, dried over magnesium sulfate, and evaporated. The obtained residue was dissolved into 3 ml of THF, to which a solution of 1M/L tetra-n-butylammonium fluoride dissolved into 1.1 ml of THF was added. The resulting solution was stirred for 10 min. and poured into ethyl actate, which was washed with 1N—HCl, water, and saturated brine, dried over magnesium sulfate, and evaporated. The obtained residue was separated by using silica gel chromatography (toluene:ethyl acetate=1:1) and recrystallized from dichloromethane-n-hexane, whereby 205 mg of the objective compound was obtained in 57% yield. The physical constants are described on Table 1.

EXAMPLE 5

N-(N-methoxycarbamoyl)-3-(3,5-di-tert-butyl-4-hydroxybenzylidene)pyrrolidin-2-one (Ia-5)

3-(3,5-Di-tert-butyl-4-hydroxybenzylidene)pyrrolidin-2-one (500 mg, 1.66 mmole) and N-methoxyphenylcarbamate (554 mg, 3.32 mmole) which was prepared according to the method described in J. Org. Chem., 21, p660, 1956, were dissolved into 8 ml of pyridine, then the solution was heated under reflux for 12 hours. The reaction solution was evaporated and the residue was dissolved into ethyl acetate, which was washed with 0.1N-HCl, water and saturated brine, dried over magnesium sulfate, and evaporated. The obtained residue was separated by using silica gel chromatography (toluene:ethyl acetate=10:1) and recrystallized from dichloromethane-n-hexane, whereby 450 mg of the objective compound was obtained in 72% yield. The physical constants are described on Table 1.

EXAMPLE 6

N-(N-hydroxy-N-methylcarbamoyl)-3-(3,5-di-tert-butyl-4-hydroxybenzylidene)pyrrolidin-2-one (Ia-6)

To a solution of 3-(3,5-di-tert-butyl-4-hydroxybenzylidene)pyrrolidin-2-one (500 mg, 1.66 mmole) dissolved into 5 ml of DMF, NaH (60% in mineral oil, 200 mg, 5 mmole) was added under ice-cooling. The mixture was stirred at room temperature for 30 min. and cooled again, then N-hydroxy-N-methylphenylcarbamate-O-tert-butylsilylether (550 mg, 1.96 mmol) which was prepared according to the method described in J. Org. Chem., 21, p660, 1956 was added thereto, and the resulting mixture was stirred at room temperature for 2 hours. The reaction mixture was poured into ethyl acetate, which was washed with 0.1N—HCl, water, and saturated brine, dried over magnesium sulfate, and evaporated. The obtained residue was separated by using silica gel chromatography (toluene:ethyl acetate=50:1) and recrystallized from dichloromethane-n-hexane, whereby 380 mg of the objective compound was obtained in 61% yield. The physical constants are described on Table 1.

EXAMPLE 7

N-carbamoyl-5-(3,5-di-tert-butyl-4-hydroxy-benzylidene)thiazolidin-4-one (Ib-1)

5-(3,5-Di-tert-butyl-4-hydroxybenzylidene)thiazolidin-4-one (479 mg, 1.5 mmole) described in Kokai 62-42977 was suspended in dried toluene (3 ml), to which chlorosulfonyl isocyanate (144 μl; 1.65 mmole) was added with stirring under nitrogen atmosphere, to obtain a transparent solution of orange color. Furthermore, the solution was heated at 90° C. for 10 min., from which toluene was evaporated under reduced pressure, then 3.6 ml of mixed solution of acetic acid and water (2:1) was added thereto. The resulting mixture was heated at 90° C. for 10 min. and poured into ice-water, which was subjected to extraction with dichloromethane. The obtained organic layer was washed with water and saturated brine, dried over magnesium sulfate, and evaporated. The obtained residue was separated by using silica gel chromatography (chloroform:acetone=20:1), whereby 377 mg of the objective compound was obtained, which was recrystallized from ethanol-ether in 53% yield. The physical constants are described on Table 1.

EXAMPLE 8

N-(N-hydroxycarbamoyl)-5-(3,5-di-tert-butyl-4-hydroxybenzylidene)thiazolidin-4-one (Ib-2)

To a solution of 5-(3,5-di-tert-butyl-4-hydroxybenzylidene)thiazolidin-4-one (319 mg, 1 mmole) dissolved into dried pyridine (5 ml), N-hydroxyphenylcarbamate-O-tert-butyldimethylsilylether (419 mg, 1.57 mmole) was added under nitrogen atmosphere with stirring, and the mixture was heated under reflux for 5.5 hours, then pyridine was evaporated under reduced pressure. An aqueous solution containing 1N hydrochloric acid was added to the obtained residue, which was extracted with ethyl acetate, washed with 1N hydrochloric acid and saturated brine, dried over sodium sulfate, and evaporated. The obtained residue was dissolved into 3 ml of THF, to which a solution of 1M/L of tetra-n-butylammonium fluoride dissolved into 1.1 ml of THF was added under ice-cooling. The mixture was stirred for 10 min. and poured into ice-water, which was subjected to extraction with dichloromethane. The organic layer was washed with water, dried over sodium sulfate, and evaporated. The obtained residue was separated by using silica gel chromatography (toluene:ethyl acetate=1:1), whereby 149 mg of the objective compound and 157 mg of the material were recovered, and the former was recrystallized from ether-n-hexane. Yield 36%. The physical constants are described on Table 1.

EXAMPLE 9

N-(N-hydroxy-N-methylcarbamoyl-5-(3,5-di-tert-butyl-4-hydroxybenzylidene)thiazolidin-4-one (Ib-3)

To a solution of 5-(3,5-di-tert-butyl-4-hydroxybenzylidene)thiazolidin-4-one (319 mg, 1 mmole) dissolved into dried DMF (3 ml), NaH (60% in mineral oil, 120 mg, 300 mmole) was added under nitrogen atmosphere with stirring under ice-cooling. The resulting mixture was warmed to room temperature and stirred for 30 min., then N-hydroxy-N-methylphenylcarbamate-O-tert-butyldimethylsilylether (422 mg, 1.5 mmole) was added thereto under ice-cooling with stirring. The mixture was stirred at room temperature for 18 hours, then which was poured into ice-water containing 1N hydrochloric acid, extracted with ethyl acetate, washed with water and saturated brine, dried over sodium sulfate, and evaporated. The obtained residue was separated by using silica gel chromatography (toluene:ethyl acetate=1:1), whereby 195 mg of the objective compound was obtained, which was recrystallized from ether-n-hexane in 29% yield. The physical constants are described on Table 1.

EXAMPLE 10

N-(N-methoxy-N-methylcarbamoyl-3-(3,5-di-tert-butyl-4-hydroxybenzylidene)pyrrolidin-2-one (Ia-7)

To a solution of 3-(3,5-di-tert-butyl-4-hydroxybenzylidene)pyrrolidin-2-one (301 mg, 1 mmole) dissolved into DMF, NaH (60% in mineral oil, 90 mg, 2.25 mmole) was added under ice-cooling. The resulting mixture was stirred at room temperature for 30 min. and cooled again, then N-methoxy-N-methylphenylcarbamate (200 mg, 1.1 mmole) was added thereto and the mixture was stirred at room temperature for 1 hour. The reaction mixture was poured into ethyl acetate, which was washed with an aqueous solution of 0.1N hydrochloric acid, water, and saturated brine, dried over magnesium sulfate, and evaporated. The obtained residue was separated by using silica gel chromatography (toluene:ethyl acetate=20:1), recrystallized from dichloromethane-n-hexane, whereby 218 mg of the objective compound was obtained in 56% yield. The physical constants are described on Table 1.

EXAMPLE 11

N-(N-ethyl-N-hydroxycarbamoyl-3-(3,5-di-tert-butyl-4-hydroxybenzylidene)pyrrolidin-2-one (Ia-8)

3-(3,5-Di-tert-butyl-4-hydroxybenzylidene)pyrrolidin-2-one (301 mg, 1.0 mmole) was dissolved into THF (5 ml), which was cooled in the acetone-Dry Ice bath, and a solution of 1.0 M/L lithium-bis(trimethylsilyl)amide dissolved into THF (2.4 ml) was added thereto. Furthermore, N-ethyl-N-hydroxyphenylcarbamate-O-tert-butyldimethylsilylether (443 mg, 1.5 mmole), which was prepared according to the method described in J. Org. Chem., 21, P660, 1956, was added thereto, then the mixture was stirred at room temperature for 1 hour. The reaction mixture was poured into ethyl acetate, washed with an aqueous solution of 0.1N hydrochloric acid, water, and saturated brine, dried over magnesium sulfate, and evaporated. The obtained residue was dissolved into acetonitrile (4 ml), to which a solution of 10 ml of hydrogen fluoride-acetonitrile (an aq. 46% HF:acetonitrile=1:19) was added and the mixture was stirred for 10 min. The reaction mixture was evaporated, then the obtained residue was dissolved into ethyl acetate, which was washed with a saturated aq. sodium bicarbonate, water, and saturated brine, dried over magnesium sulfate, and evaporated. The obtained residue was separated by using silica gel chromatography (n-hexane:ethyl acetate=5:1) and recrystallized from dichloromethane-n-hexane, whereby 353 mg of the objective compound was obtained in 92% yield. The physical constants are described on Table 1.

EXAMPLE 12

N-(N-isopropyl-N-hydroxycarbamoyl)-3-(3,5-di-tert-butyl-4-hydroxybenzylidene)pyrrolidin-2-one (Ia-9)

3-(3,5-Di-tert-butyl-4-hydroxybenzylidene)pyrrolidin-2-one (301 mg, 1.0 mmole) was dissolved into THF (10 ml), which was cooled in the acetone-Dry Ice bath, and a solution of 1.0 M/L lithium-bis(trimethylsilyl)amide dissolved into THF (2.4 ml) was added thereto. Furthermore, N-hydroxy-N-isopropylphenylcarbamate-O-tert-butyldimethylsilylether (402 mg, 1.3 mmole), which was prepared according to the method described in J. Org. Chem., 21, P660, 1956, was added thereto, then the resulting mixture was stirred at room temperature for 3 hours. The reaction mixture was poured into ethyl acetate, washed with aq. 0.1N hydrochloric acid, water, and saturated brine, dried over magnesium sulfate, and evaporated. The obtained residue was dissolved into acetonitrile (4 ml), to which a solution of 10 ml of hydrogen fluoride-acetonitrile (aq. 46% HF:acetonitrile=1:19) was added and the mixture was stirred for 10 min. The reaction mixture was evaporated, then the obtained residue was dissolved into ethyl acetate, which was washed with aq. saturated sodium bicarbonate, water, and saturated brine, dried over magnesium sulfate, and evaporated. The obtained residue was separated by using silica gel chromatography (n-hexane:ethylacetate=5:1), and recrystallized from dichloromethane-n-hexane, whereby 102 mg of the objective compound was obtained in 25.4% yield. The physical constants are described on Table 1.

EXAMPLE 13

(1) The Preparation of 5-(3,5-di-tert-butyl-4-hydroxybenzylidene)oxazolidin-4-one 5-(3,5-Di-tert-butyl-4-hydroxybenzylidene)-2-oxazolidin-4-one (4.64 g, 13.9 mmole), which was prepared according to the method described in Kokai 2-62864, was dissolved into dried ethanol (140 ml), to which Raney nickel (about 46 g) was added, then the resulting mixture was refluxed under nitrogen atmosphere with stirring for 1.5 hours. Raney nickel was removed by filtration, and the residue was washed with dichloromethane, then the solvent was evaporated. The obtained residue was separated by using silica gel chromatography (toluene:ethyl acetate=1:1), and crystallized from dichloromethane-n-hexane, whereby the objective compound was obtained.

Mp. 213°–217° C.

Elementary Analysis (%) for $C_{18}H_{25}NO_3$

Calcd.: C:71.25, H:8.31, N:4.622.
Found: C:70.73, H:8.21, N:4.58.
IR(KBr) $\nu$ max cm$^{-1}$: 3616, 3382, 3208, 1696.
NMR(CDCl$_3$) $\delta$ ppm: 1.47(s,18H), 5.37(3,1H), 5.52(s,2H), 6.25(s,1H), 7.55 (s,2H), 8.05(b.s,1H).

(2)
N-carbamoyl-5-(3,5-di-tert-butyl-4-hydroxybenzylidene)oxazolidin-4-one (Ic-1)

To a suspension of 5-(3,5-di-tert-butyl-4-hydroxybenzylidene)oxazolidin-4-one (100 mg, 0.33 mmole) suspended in dried toluene (0.5 ml), 32 μl of chlorosulfonyl isocyanate (0.363 mmole) was added under nitrogen atmosphere with stirring and the mixture was dissolved for 2 min. After the solution colored to brown, it was heated at 90° C. for 10 min. and toluene was evaporated under reduced pressure. A mixed solution (0.8 ml) of acetic acid and water (2:1) was added thereto, and the mixture was heated at 90° C. under nitrogen atmosphere for 10 min. The resulting mixture was poured into ice-water, which was subjected to extraction with dichloromethane, then the organic layer was washed with water, dried over sodium sulfate, and evaporated. The obtained residue was separated by using silica gel chromatography (toluene:ethyl acetate=1:1), and recrystallized from ether-n-hexane, whereby 73 mg of the objective compound was obtained in 64% yield. The physical constants are described on Table 1.

EXAMPLE 14

The Preparation of N-(N-hydroxycarbamoyl)-5-(3,5-di-tert-butyl-4-hydroxybenzylidene)oxazolidin-4-one (Ic-2)

To a solution of 5-(3,5-di-tert-butyl-4-hydroxybenzylidene)oxazolidin-4-one (100 mg, 0.33 mmole) dissolved into dried pyridine (1.7 ml), N-hydroxyphenylcarbamate-O-tert-butyldimethylsilylether (0.5 mmole) was added under nitrogen atmosphere with stirring, and the mixture was heated under reflux for 7 hours, then pyridine was evaporated under reduced pressure. Ice-water containing 2N—HCl was added to the obtained residue, which was subjected to extraction with ethyl acetate, then the organic layer was washed with water, dried over sodium sulfate, and evaporated. The obtained residue was dissolved into THF (1.5 ml), to which a solution of 1M tetra-n-butylammonium fluoride dissolved into THF (500 μl, 0.5 mmole) was added under ice-cooling with stirring. The mixture was stirred for 10 min. and poured into ice-water, which was subjected to extraction with dichloromethane. The organic layer was washed with water, dried over sodium sulfate, and evaporated. The obtained residue was separated by using silica gel chromatography (toluene:ethyl acetate=1:1), and recrystallized from dichloromethane-n-hexane, whereby 19 mg of the objective compound was obtained in 16% yield. The starting material (63 mg) was recovered. The physical constants are described on Table 1.

EXAMPLE 15

N-(N-hydroxy-N-methylcarbamoyl)-5-(3,5-di-tert-butyl-4-hydroxybenzylidene)oxazolidin-4-one (Ic-3)

To a solution of 5-(3,5-di-tert-butyl-4-hydroxybenzylidene)oxazolidin-4-one (100 mg, 0.33 mole) dissolved into dried DMF (1 ml), sodium hydride (60% in meneral oil) was added under nitrogen atmosphere, under ice-cooling with stirring, then the solution was warmed to room temperature and stirred for 30 min. The resulting mixture was again cooled with ice, to which N-hydroxy-N-methylcarbamate-O-tert-butyldimethylsilyl ether (139 mg, 0.5 mmole) was added, then the mixture was stirred under nitrogen atmosphere at room temperature for 20 hours and poured into ice-water containing 3 ml of 2N hydrocloric acid. The resulting mixture was subjected to extraction with ethyl acetate, then the extract was washed with water, dried over sodium sulfate, and evaporated. The obtained residue was separated by using silica gel chromatography (toluene:ethyl acetate=4:1), whereby 35 mg of the objective compound was obtained in 28% yield. The material (31 mg) was recovered. The physical constants are described on Table 1.

EXAMPLE 16

1-(N-benzyloxycarbamoyl)-3-(3,5-di-tert-butyl-4-hydroxybenzylidene)pyrrolidin-2-one (Ia-10)

3-(3,5-Di-tert-butyl-4-hydroxybenzylidene)pyrrolidin-2-one (600 mg, 2 mmole) and phenyl N-benzyloxycarbamate (490 mg, 2.01 mmole) were dissolved into 8 ml of pyridine and the solution was heated under reflux for 12 hours. The reaction mixture was evaporated and the obtained residue was dissolved into ethyl acetate, which was washed with an aqueous solution of 0.1N hydrochloric acid, water, and saturated brine, dried over magnesium sulfate, and evaporated. The obtained residue was separated by using silica gel chromatography (toluene:ethyl acetate=10:1) and recrystallized from dichloromethane/n-hexane, whereby 550 mg of the objective compound (Ia-10) was obtained in 61% yield.

Mp.: 164°–165° C.

Elementary Analysis (%) for $C_{27}H_{34}N_2O_4$

Calcd.: C,71.97; H,7.61; N,6.22.
Found: C,71.99; H,7.66; N,6.29.
I R (KBr) cm$^{-1}$: 3550,3256,1704, 1632, 1593.
NMR(CDCl$_3$)$\delta$: 1.46 (18H,s); 3.07 (2H,d.t,J=2.6,7.1 Hz); 3.95 (2H, t, J=7.1 Hz); 5.0 (2H,s); 5.57 (1H,s); 7.35–7.49 (8H, m); 10.97 (1H,s).

EXAMPLE 17

1-(N-benzyloxy-N-methylcarbamoyl)-3-(3,5-di-tert-butyl-4-hydroxybenzylidene)pyrrolidin-2-one (Ia-11)

3-(3,5-Di-tert-butyl-4-hydroxybenzylidene)pyrrolidin-2-one (3.01 g, 10 mmole) was dissolved into THF (60 ml), which was cooled to −70° C. To this mixture, a solution of 1.0M lithium bis(trimethylsilyl)amide dissolved into THF (24 ml) was added. Furthermore, N-benzyloxy-N-methylphenylcarbamate (2.9 g, 12 mmole) was added thereto and the mixture was stirred at room temperature for 1 hour. The reaction mixture was poured into ethyl acetate, which was washed with an aqueous solution of 0.1N hydrochloric acid, water, and saturated brine, dried over magnesium sulfate, and evaporated. The obtained residue was separated by using silica gel chromatography (toluene:ethyl acetate=10:1), whereby 1.5 g of the objective compound (Ia-11) was obtained as white amorphous in 32% yield.

Elementary Analysis (%) for $C_{27}H_{34}N_2O_4$

Calcd.: C,72.39; H,7.81; N,6.03.
Found: C,72.51; H,7.79; N,5.94.
IR (KBr) cm$^{-1}$: 3610, 2950, 2860, 1705, 1644.
NMR (CDCl$_3$)δ: 1.47 (18H,s); 3.03 (2H,d.t,J=2.6, 7.0 Hz); 3.26 (3H,s); 3.75 (2H,t,J=7.0); 4.98 (2H,s); 5.52 (1H,s); 7.34–7.48 (8H,m).

EXAMPLE 18

1-(N-ethoxy-N-methylcarbamoyl)-3-(3,5-di-tert-butyl-4-hydroxybenzylidene)pyrrolidin-2-one (Ia-12)

Substantially in the same manner as in Example 17, 3-(3,5-di-tert-butyl-4-hydroxybenzylidene)pyrrolidin-2-one (3.50 g, 11.6 mmole) and N-ethoxy-N-methylphenylcarbamate (3.4 g, 17.4 mmole) were treated to obtain products, which were purified, and crystallized from isopropyl ether/n-hexane, whereby the objective compound (Ia-12) 2.80 g was obtained in 60% yield.
Mp.: 113°–114° C.

Elementary Analysis (%) for $C_{23}H_{34}N_2O_4 \cdot H_2O$

Calcd.: C,65.69; H,8.63; N,6.66.
Found: C,65.89; H,8.18; N,6.79.
NMR (CDCl$_3$)δ: 1.28 (3H, t, J=7.0 Hz); 1.46 (18H, s); 3.09 (2H, dt, J=7.4, 2.6 Hz); 3.87 (2H, t, J=7.4 Hz); 4.06 (2H, q, J=7.0 Hz); 5.53 (1H, s); 7.36 (2H, s); 7.43(1H, t, J=2.6 Hz).

EXAMPLE 19

1-(N-isopropoxy-N-methylcarbamoyl)-3-(3,5-di-tert-butyl-4-hydroxybenzylidene)pyrrolidin-2-one (Ia-13)

According to the same method as in Example 17, 3-(3,5-di-tert-butyl-4-hydroxybenzylidene)pyrrolidin-2-one (2.74 g, 9.1 mmole) and N-isopropoxy-N-methylphenylcarbamate (2.86 g, 13.7 mmole) were treated to obtain products, which were purified and crystallized from isopropyl ether/n-hexane, whereby the objective compound (Ia-13) 1.80 g was obtained in 47% yield.
Mp.: 104°–106° C.
NMR (CDCl$_3$)δ: 1.29 (6H,d,J=5.8 Hz); 1.46 (18H,s); 3.09 (2H,dt,J=7.4,2.4 Hz); 3.30 (3H,s); 3.87 (2H,t,J=7.4 Hz); 4.29 (1H,sept.J=5.8 Hz); 5.53 (1H,s);7.36 (2H,s); 7.43 (1H,t,J=2.4 Hz).

EXAMPLE 20

1-(N-isopropyl-N-methoxycarbamoyl)-3-(3,5-di-tert-butyl-4-hydroxybenzylidene)pyrrolidin-2-one (Ia-14)

According to the same method as in Example 17, 3-(3,5-di-tert-butyl-4-hydroxybenzylidene)pyrrolidin-2-one (602 mg, 2.0 mmole) and N-isopropyl-N-methoxyphenylcarbamate (628 mg, 3 mmole) were treated to obtain products, which were purified and crystallized from isopropyl ether/n-hexane, whereby the objective compound (Ia-14) 643 mg was obtained in 77% yield.
Mp.: 83°–85° C.
NMR (CDCl$_3$)δ: 1.31 (6H,d,J=6.6 Hz); 1.46 (18H,s); 3.08 (2H,dt,J=7.4,2.8 Hz); 3.78 (3H,s); 3.89 (2H,t,J=7.4 Hz); 4.10 (1H,sept.J=6.6 Hz); 5.52 (2H,s); 7.35 (2H,s); 7.44 (1H,t,J=2.8 Hz).

EXAMPLE 21

1-morpholinocarbonyl-3-(3,5-di-tert-butyl-4-hydroxybenzylidene)pyrrolidin-2-one (Ia-15)

To a solution of 3-(3,5-di-tert-butyl-4-hydroxybenzylidene)pyrrolidin-2-one (241 mg, 0.8 mmole) dissolved into DMF (2.4 ml), sodium hydride (60% in mineral oil, 96 mg, 2.4 mmole) was added under ice-cooling under nitrogen atmosphere with stirring for 30 min. Morpholinophenyl carbamate (249 mg, 1.2 mmole) was added thereto and the mixture was allowed to stand at room temperature for 4 hours. The reactant was poured into ice-water, and extracted with ethyl acetate. The organic layer was washed with water, dried over magnesium sulfate, and evaporated. The obtained residue was recrystallized from dichloromethane/ether, whereby 300 mg of the objective compound (Ia-15) was obtained in 90% yield.
Mp.: 212.5°–213.5° C.

Elementary Analysis (%) for $C_{24}H_{34}N_2O_4$

Calcd.: C,69.53; H,8.27; N,6.76.
Found: C,69.36; H,8.38; N,6.67.
IR (KBr) cm$^{-1}$: 3590,3440,1688,1644,1633,1596.
NMR (CDCl$_3$)δ: 1.48 (18H,s); 3.09 (2H,d.t,J=2.5,7.1 Hz); 3.56 (4H,bs); 3.77 (6H,m); 5.53 (1H,s); 7.36 (2H,s); 7.41 (1H,t,J=2.5 Hz).

EXAMPLE 22

1-(N-acetoxy-N-methylcarbamoyl)-3-(3,5-di-tert-butyl-4-hydroxybenzylidene)pyrrolidin-2-one (Ia-16)

To a solution of 1-(N-hydroxy-N-methylcarbamoyl)-3-(3,5-di-tert-butyl-4-hydroxybenzylidene)pyrrolidin-2-one (Ia-6) (222 mg, 0.6 mmole) dissolved into pyridine (3 ml), 1.8 ml of acetic anhydride was added and the mixture was stirred at room temperature for 5 hours, then the resulting mixture was evaporated. Hydrochloric acid (0.5N) was added thereto, and the mixture was subjected to extraction with dichloromethane. The organic layer was washed with water, sodium bicarbonate, and water in order, dried over magnesium sulfate, and evaporated. The obtained residue was recrystallized from dichloromethane/ether, whereby 211 mg of the objective compound (Ia-16) was obtained in 84% yield.
Mp. 175°–176° C.

Elementary Analysis (%) for $C_{23}H_{32}N_2O_5 \cdot \frac{1}{4}H_2O$

Calcd.: C,65.61; H,7.78; N,6.65.
Found: C,65.79; H,7.85; N,6.66.
IR(KBr) cm$^{-1}$: 3595,3440,1797,1711,1688,1638,1596.
NMR(CDCl$_3$) δ: 1.46 (18H,s); 2.14 (3H,s); 3.10 (2H,d.t,J=2.6,7.3 Hz); 3.37 (3H,s); 3.88 (2H,t,J=7.4 Hz);5.54 (1H,s); 7.36 (2H,s); 7.46 (1H,t, J=2.8 Hz).

EXAMPLE 23

1-(N-acetoxycarbamoyl)-3-(3,5-di-tert-butyl-4-hydroxybenzylidene)pyrrolidin-2-one (Ia-17)

N-(N-Hydroxycarbamoyl)-3-(3,5-di-tert-butyl-4-hydroxybenzylidene)pyrrolidin-2-one (Ia-4)(2 g, 5.55 mmole), acetic anhydride (680 mg, 6.66 mmole), and pyridine (10 ml) were reacted according to the same method as in Example 22, whereby 1.35 mg of the objective compound (Ia-17) was obtained in 60.5% yield.
Mp.: 165°–166° C.

Elementary Analysis (%) for $C_{22}H_{30}N_2O_5$

Calcd.: C,65.65; H,7.51; N,6.96.
Found: C,65.39; H,7.50; N,6.81.
IR(KBr) cm$^{-1}$: 3600, 3300, 2950, 1800, 1708, 1689, 1631, 1592.
NMR(CDCl$_3$) δ: 1.47 (18H,s); 2.26 (3H,s); 3.11 (2H,d.t,J=2.6, 7.3 Hz); 3.35 (3H,s); 3.95 (2H,t,J=7.3); 5.60 (1H,s); 7.38 (2H,s); 7.51 (1H,t, J=2.6 Hz) 11.44 (1H,s).

EXAMPLE 24

3-(N-methoxy-N-methylcarbamoyl)-5-(3,5-di-tert-butyl-4-hydroxybenzylidene)thiazolidin-4-one (Ib-4)

To a solution of 5-(3,5-di-tert-butyl-4-hydroxybenzylidene)thiazolidin-4-one (319 mg, 1 mmole), which was described in Kokai 62-42977, dissolved into DMF (3 ml), sodium hydride (60% in mineral oil, 120 mg, 3 mmole) was added under ice-cooling, then N,O-dimethylhydroxyphenylcarbamate (272 mg, 1.5 mmole) was added thereto and the mixture was stirred at room temperature for 2.5 hours. The reaction mixture was poured into 1N HCl, which was subjected to extraction with ethyl acetate. The extract was washed with water, dried over magnesium sulfate, and evaporated. The obtained residue was separated and purified by using silica gel chromatography (toluene:ethyl acetate=1:1), then lyophilized from benzene, whereby 275 mg of the objective compound (Ib-4) was obtained in 68% yield.

IR(KBr) cm$^{-1}$: 3610, 3560, 1700.
NMR(CDCl$_3$) δ: 1.47 (18H,s); 3.31 (3H,s); 3.81(3H,s); 4.87 (2H,s); 5.52 (1H,s); 7.40 (2H,s); 7.54 (1H,s).

EXAMPLE 25

3-(N-methoxy-N-methylcarbamoyl)-5-(3,5-di-tert-butyl-4-hydroxybenzylidene)oxazolidin-4-one (Ic-4)

5-(3,5-Di-tert-butyl-4-hydroxybenzylidene)oxazolidin-4-one (303 mg, 1 mmole) was reacted and treated under the similar condition as in Example 24, then the reaction mixture was separated by using silica gel chromatography (toluene:ethyl acetate=1:1), then lyophilized from benzene, whereby 90 mg of the objective compound (Ic-4) was obtained in 23% yield.

Elementary Analysis (%) for $C_{21}H_{30}N_2O_5$

Calcd.: C,64.59; H,7.74; N,7.17.
Found: C,64.65; H,7.63; N,6.89.
IR (KBr) cm$^{-1}$: 3620, 3540, 3440, 1738, 1700.
NMR (CDCl$_3$) δ: 1.45(18H,s), 3.30(3H,s), 3.81(3H,s), 5.42(1H,s), 5.70 (2H,s), 6.39(1H,s), 7.54(2H,s).

EXAMPLE 26

(1) 1-Ethoxycarbonyl-5,5-dimethylpyrrolidin-2-one

To a suspension of 1.43 g (35.8 mmol) of NaH (60% in mineral oil) in 12 ml of DMF was dropwise added over 35 minutes a solution of 1.35 g (11.93 mmol) of 5,5-dimethylpyrrolidin-2-one in 24 ml of DMF while being stirred under ice-cooling. After 30 minutes, 1.7 ml (17.5 mmol) of ethyl chlorocarbonate was added to the mixture and allowed to stand at room temperature for 2 hours. The reaction mixture was extracted with ethyl acetate and the organic layer was washed with saturated brine then dried over magnesium sulfate and evaporated to give 1.746 g of the objective compound as oil.

IR (CHCl$_3$) cm$^{-1}$: 1782, 1714.

NMR (CDCl$_3$) δ: 1.31(6H,s), 1.38(3H,t,J=7 Hz), 1.84~2.04(2H,m), 2.39~2.55 (2H,m), 4.34(2H,q,J=7 Hz).

(2)
3-(3,5-Di-tert-butyl-4-hydroxybenzylidene)-5,5-dimethylpyrrolidin-2-one

To a chilled solution (−70° C.) of 1.657 g (8.95 mmol) of the thus obtained 1-ethoxycarbonyl-5,5-dimethylpyrrolidin-2-one in THF (45 ml) was added 9 ml of a THF solution of 1.0M lithium hexamethydisilazane under a nitrogen atmosphere. Five minutes later, 2.74 g (9 mmol) of 3,5-di-tert-butyl-4-trimethylsiloxybenzaldehyde was added thereto and the mixture was stirred at room temperature for 2 hours. The reaction mixture was then poured into ice-water and extracted with dichloromethane. The dichloromethane layer was washed with water, dried over magnesium sulfate and evaporated to give a residue, which was then dissolved in 40 ml of toluene and combined with 280 mg of p-toluenesulfonic acid and the mixture was refluxed for 1.5 hours. After cooled down, the reaction mixture was evaporated and the resulting residue was dissolved in 30 ml of THF. Under ice-cooling, 3.5 ml of a THF solution of 2.0M tetra-n-butylammonium fluoride was added thereto and the mixture was stirred for 10 minutes. The mixture was poured into ice-water containing sodium bicarbonate and extracted with dichloromethane. The dichloromethane layer was washed with an aq. sodium bicarbonate, water, then saturated brine and dried over magnesium sulfate and evaporated to give 1-ethoxycarbonyl-3-(3,5-di-tert-butyl-4-hydroxybenzylidene)-5,5-dimethylpyrrolidin-2-one as residue, which was then dissolved in a methanol/water (4/1) mixed solution (100 ml). Five % solution of potassium hydroxide (5 ml) was added thereto while being stirred under ice-cooling and stirred at room temperature for 3.5 hours. The reaction mixture was neutralized with 38 ml of 2N hydrochloric acid and extracted with dichloromethane. The organic layer was washed with saturated brine, dried over magnesium sulfate and evaporated to give a residue, which was recrystallized from a dichloromethane/ether mixture to give 386 mg of the objective compound. Then the mother liquor was chromatographed on silica gel (toluene/ethyl acetate=1/1) and recrystallized to give 559 mg of the objective compound. Totally, 945 mg of the objective compound was obtained in 24% overall yield.

m.p. 239°-242° C.

Elementary Analysis (%) for $C_{21}H_{31}NO_2$

Calcd.: C,76.55; H,9.48; N,4.25.
Found: C,76.13; H,9.47; N,4.29.
IR (KBr) cm$^{-1}$: 3400, 3160, 1679, 1637, 1592.
NMR (CDCl$_3$) δ: 1.36 (6H,s); 1.46 (18H,s); 2.91 (2H,d,J=2.8 Hz); 5.45 (1H, s); 6.07 (1H, bs); 7.32 (2H,s); 7.33 (1H,t,J=2.8 Hz).

(3)
1-Carbamoyl-3-(3,5-di-tert-butyl-4-hydroxybenzylidene)-5,5-dimethylpyrrolidin-2-one (Id-1)

To a suspension of 329 mg (1 mmol) of the thus obtained 3-(3,5-di-tert-butyl-4-hydroxybenzylidene)-5,5-dimethylpyrrolidin-2-one in 2 ml of dry toluene was added 96 μl (1.1 mmol) of chlorosulfonyl isocyanate under a nitrogen atmosphere. The reaction mixture was heated at 90° C. for 10 minutes and evaporated to give a residue, which was added with 2.4 ml of acetic acid/water (2/1) and heated at 90° C. for 10 minutes. The reaction mixture was then poured into ice-water and extracted with dichloromethane three times. The organic layers were collected and washed with water, dried over magnesium sulfate and then evaporated to give a residue, which was chromatographed on silica gel (toluene/ethyl acetate=1/1) and recrystallized from ether to give 107 mg of the objective compound (Id-1) in 29% yield.

m.p. 200°-203° C.

Elementary Analysis (%) for $C_{22}H_{32}N_2O_3.\frac{1}{2}H_2O$

Calcd.: C,69.26; H,8.72; N,7.34.
Found: C,68.96; H,8.49; N,7.32.
IR (KBr) cm$^{-1}$: 3560, 3360, 1715, 1637, 1592.
NMR (CDCl$_3$) δ: 1.47(18H,s); 1.64(6H,s); 2.89(2H,d,J=2.6 Hz); 5.16(1H,bs); 5.56(1H,s); 7.34(2H,s); 7.52(1H,t,J=2.6 Hz); 8.82(1H,bs).

EXAMPLE 27

1-(N-Hydroxycarbamoyl)-3-(3,5-di-tert-butyl-4-hydroxybenzylidene)-5,5-dimethylpyrrolidin-2-one (Id-2)

Substantially in the same manner as in Example 17, 329 mg (1 mmol) of 3-(3,5-di-tert-butyl-4-hydroxybenzylidene)-5,5-dimethylpyrrolidin-2-one and 443 mg (1.5 mmol) of N-hydroxyphenylcarbamate-O-tert-butyldimethylsilyl ether were treated to give a residue, which was chromatographed on silica gel (toluene/ethyl acetate=1/1) and lyophilized from benzene to give 89 mg of the objective compound (Id-2) as powder in 24% yield.

Elementary Analysis (%) for $C_{22}H_{32}N_2O_4$

Calcd.: C,68.01; H,8.30; N,7.21.
Found: C,68.19; H,8.38; N,6.96.
IR (KBr) cm$^{-1}$: 3616, 3260, 1704, 1635, 1594.
NMR (CDCl$_3$) δ: 1.47(18H,s); 1.65(6H,s); 2.92(2H,d,J=2.6 Hz); 5.57(1H,s); 6.79(1H,bs); 7.33(2H,s); 7.49(1H,t,J=5.2 Hz); 11.01(1H,s).

EXAMPLE 28

(1)

1-(N-Methoxy-N-methylcarbamoyl)-5,5-dimethylpyrrolidin-2-one

To a solution of 566 mg (5 mmol) of 5,5-dimethylpyrrolidin-2-one in 15 ml of DMF was added 600 mg (15 mmol) of NaH (60% in mineral oil) while being stirred under ice-cooling under a nitrogen atmosphere. Thirty minutes later, 1.359 g (7.5 mmol) of N,O-dimethylhydroxyphenyl carbamate was added thereto, and the reaction mixture was stirred at room temperature for 22 hours. The reaction mixture was poured into ice-water and extracted with ethyl acetate. The organic layer was washed with water, dried over magnesium sulfate and evaporated to give a residue, which was chromatographed on silica gel (toluene/ethyl acetate=1/1) to give 453 mg of the objective compound as oil.

IR (CHCl$_3$) cm$^{-1}$: 1710, 1686.
NMR (CDCl$_3$) δ: 1.48(6H,s); 1.92(2H,t,J=7.7 Hz); 2.49(2H,t,J=7.7 Hz); 3.23 (3H,s); 3.75(3H,s).

(2)

1-(N-Methoxy-N-methylcarbamoyl)-3-(3,5-di-tert-butyl-4-hydroxybenzylidene)-5,5-dimethylpyrrolidin-2-one (Id-3)

To a chilled solution (−70° C.) of 453 mg (2.26 mmol) of the thus obtained 1-(N-methoxy-N-methylcarbamoyl)-5,5-dimethylpyrrolidin-2-one in THF (12 ml) was added 2.26 ml (2.26 mmol) of a THF solution of 1.0M lithium hexamethyldisilazane while being stirred under a nitrogen atmosphere. Five minutes later, 693 mg (2.26 mmol) of 3,5-di-tert-butyl-4-trimethylsiloxybenzaldehyde was added thereto and the mixture was warmed to room temperature and stirred for 2 hours. The reaction mixture was then poured into ice-water and extracted with dichloromethane. The dichloromethane layer was washed with water, dried over magnesium sulfate and evaporated to give a residue, which was then dissolved in 23 ml of toluene. To the mixture was added 145 mg of p-toluenesulfonic acid, which was refluxed for 1.5 hours. The solvent was removed under reduced pressure to give a residue, which was dissolved in 13 ml of THF and stirred under ice-cooling. To the reaction mixture was added 1 ml of a THF solution of 2.0M tetra-n-butylammonium fluoride, which was stirred for 10 minutes. The reaction mixture was poured into ice-water containing sodium bicarbonate and extracted with dichloromethane. The dichloromethane layer was washed with an aq. sodium bicarbonate and water, dried over magnesium sulfate and evaporated to give a residue, which was then chromatographed on silica gel (toluene/ethyl acetate=9/1) and lyophilized from benzene to give 270 mg of the objective compound (Id-3) in 29% yield.

Elementary Analysis (%) for $C_{24}H_{36}N_2O_4.\frac{1}{4}C_6H_6$

Calcd.: C,70.23; H,8.67; N,6.42.
Found: C,70.46; H,8.60; N,6.30.
IR (KBr) cm$^{-1}$: 3614, 3552, 1692, 1614, 1592.
NMR (CDCl$_3$) δ: 1.47(18H,s); 1.55(6H,s); 2.91(2H,d,J=2 Hz); 3.26(3H,s); 3.78(3H,s); 5.53(1H,s); 7.32(2H,s); 7.47(1H,s).

EXAMPLE 29

1-(N-Hydroxy-N-methylcarbamoyl)-3-(3,5-di-tert-butyl-4-hydroxybenzylidene)-5,5-dimethylpyrrolidin-2-one (Id-4)

To a solution of 1.22 g (9.17 mmol) of aluminium chloride, 1.37 g (9.17 mmol) of sodium iodide and 9.1 ml of acetonitrile was added a solution of 382 mg (0.917 mmol) of the thus obtained compound (Id-3) in Example 28 in 2.3 ml of acetonitrile. The reaction mixture was stirred at room temperature for 1.5 hours and poured into ice-water and extracted with dichloromethane. The dichloromethane layer was washed with dil. hydrochloric acid and water, dried over magnesium sulfate and evaporated to give a residue, which was recrystallized from ether/n-hexane to give 238 g of the objective compound (Id-4) in 64% yield.

m.p.: 176°-179° C.

Elementary Analysis (%) for $C_{23}H_{34}N_2O_4.\frac{1}{4}H_2O$

Calcd.: C,67.87; H,8.54; N,6.88.
Found: C,67.90; H,8.46; N,6.88.
IR (KBr) cm$^{-1}$: 3562, 1681, 1654, 1628, 1590.

NMR (CDCl$_3$) δ: 1.47(18H,s);1.61(6H,s); 2.93(2H,d,J=2.4 Hz); 3.35(3H,s); 5.56(1H,s); 7.33(2H,s); 7.51(1H,t,J=2.2 Hz); 8.80(1H,s).

EXAMPLE 30

(1) 1-Ethoxycarbonyl-5-methylpyrrolidin-2-one

Substantially in the same manner as in Example 26 (1), 3.965 g (40 mmol) of 5-methylpyrrolidin-2-one was treated to give a residue as oil, which was 6.429 g of the objective compound in 94% yield.

IR(CHCl$_3$) cm$^{-1}$: 1780, 1711, 1672(s).

NMR (CDCl$_3$) δ: 1.17(3H,d,J=6.6 Hz); 1.35(3H,t,J=7.1 Hz); 1.62-1.92(2H,m); 2.31-2.52(2H,m); 4.90(2H,q,J=7.1); 4.27-4.36(1H,m).

(2) 3-(3,5-di-tert-Butyl-4-hydroxybenzylidene)-5-methylpyrrolidin-2-one

Substantially in the same manner as in Example 26 (2), 3.424 g (20 mmol) of the thus obtained 1-ethoxycarbonyl-5-methylpyrrolidin-2-one was treated to give a residue, which was chromatographed on silica gel (toluene/ethyl acetate=1/1) and recrystallized from ether to give 1.271 g of the objective compound in 20% yield.

m.p.: 179°-181° C.

Elementary Analysis (%) for C$_{20}$H$_{29}$NO$_2$

Calcd.: C,76.15; H,9.27; N,4.44.
Found: C,75.89; H,9.15; N,4.55.

IR (KBr) cm$^{-1}$: 3630, 3200, 1690(s), 1678, 1637, 1597.

NMR (CDCl$_3$) δ: 1.32(3H,d,J=6.2 Hz), 1.46(18H,s), 2.64(1H,t.d,J=3,17.2 Hz), 3.31(1H,d.q,J=2.8,8.2,Hz), 3.87~3.94(1H,m), 5.45(1H,s), 6.51(1H,s), 7.32(1H,t,J=2.6 Hz), 7.34(2H,s).

(3) 1-Carbamoyl-3-(3,5-di-tert-butyl-4-hydroxybenzylidene)-5-methylpyrrolidin-2-one (Id-5)

Substantially in the same manner as in Example 26 (3), 221 mg (0.7 mmol) of the thus obtained 3-(3,5-di-tert-butyl-4-hydroxybenzylidene)-5-methyl-pyrrolidin-2-one was treated to give a residue, which was chromatographed on silica gel (toluene/ethyl acetate=1/1) and recrystallized from ether to give 107 mg of the objective compound (Id-5) in 43% yield.

m.p.: 195°-196° C.

Elementary Analysis (%) for C$_{21}$H$_{30}$N$_2$O$_3$

Calcd.: C,70.36; H,8.44; N,7.82.
Found: C,70.10; H,8.48; N,7.67.

IR (KBr) cm$^{-1}$: 3600, 3370, 1712, 1640, 1575.

NMR (CDCl$_3$) δ: 1.38(3H,d,J=6.4 Hz); 1.47(18H,s); 2.64(1H,t,d,J=2.2,17 Hz); 3.23(1H,d.q,J=3.2,8.7 Hz); 4.52-4.61(1H,m); 5.20(1H,bs); 5.57(1H,s), 7.37(2H,s);7.51(1H,t,J=2.7 Hz); 8.59(1H,bs).

EXAMPLE 31

1-(N-Hydroxycarbamoyl)-3-(3,5-di-tert-butyl-4-hydroxybenzylidene)-5-methylpyrrolidin-2-one (Id-6)

Substantially in the same manner as in Example 27, 473 mg (1.5 mmol) of the thus obtained 3-(3,5-di-tert-butyl-4-hydroxybenzylidene)-5-methylpyrrolidin-2-one in Example 30 (2) was treated to give a residue, which was chromatographed on silica gel (toluene/ethyl acetate=1/1) and lyophilized from benzene to give 273 mg of the objective compound (Id-6) as powder in 49% yield.

Elementary Analysis (%) for C$_{21}$H$_{30}$N$_2$O$_4$

Calcd.: C,67.35; H,8.08; N,7.48.
Found: C,67.66; H,8.07; N,7.14.

IR (KBr) cm$^{-1}$: 3610, 3400, 3250, 1700, 1630, 1593.

NMR (CDCl$_3$) δ: 1.39(3H,d,J=6.4 Hz); 1.47(18H,s); 2.67(1H,t.d,J=2,17.2 Hz); 3.28(1H,d.q,J=3,8.2 Hz); 4.51-4.60(1H,m); 5.58(1H,s); 6.80(1H,bs); 7.36 (2H,d,J=3.4 Hz); 7.49(1H,t,J=3 Hz); 10.81(1H,s).

EXAMPLE 32

(1) 2-Methoxycarbonylisoxazolidin-3-one

To a suspension of 466 mg (11.66 mmol) of NaH (60% in mineral oil) in 20 ml of DMF was dropwise added 20 ml of a DMF solution of isoxazolidin-2-one while being stirred under ice-cooling for 30 minutes. To the reaction mixture was added 858 μl (11.1 mmol) of methyl chlorocarbonate at −30° C. while being stirred under ice-cooling for 2 hours. The reaction mixture was evaporated under reduced pressure to give a residue, which was added with dichloromethane. The thus obtained suspension was filtered and the filtrate was evaporated to give a crude product, which was chromatographed on silica gel (n-hexane/ethyl acetate=2/1) to give 1.290 g of the objective compound in 80% yield.

Elementary Analysis (%) for C$_5$H$_7$NO$_4$

Calcd.: C,41.38; H,4.86; N,9.65.
Found: C,40.96; H,4.96; N,9.91.

NMR (CDCl$_3$) δ: 2.98(2H,t,J=7.8 Hz); 3.94(3H,s); 4.77(2H,t,J=7.8 Hz).

(2) 2-Methoxycarbonyl-4-(3,5-di-tert-butyl-4-hydroxybenzylidene)isoxazolidin-3-one To a chilled solution (−78° C.) of 1.55 g (7.96 mmol) of the thus obtained 2-methoxycarbonylisoxazolidin-3-one in THF (100 ml) was added 8.4 ml of a THF solution of 1.0M lithium hexamethyldisilazane, and the mixture was stirred at −78° C. for 30 minutes. To the reaction mixture was added 2.5 ml of a THF solution of 2.44 g (8.76 mmol) of 3,5-di-tert-butyl-4-hydroxybenzaldehyde-O-methoxymethyl ether and the mixture was stirred at −78° C. for 30 minutes and then 8.4 ml of 1N hydrochloric acid and ethyl acetate were added thereto. The ethyl acetate layer was washed with water and saturated brine, dried over magnesium sulfate and evaporated under reduced pressure to give a residue, which was dissolved in 200 ml of toluene and combined with 400 mg of p-toluenesulfonic acid and the mixture was refluxed under flask equipped with the Dean-Stark water separator for 3 hours. After cooled down, the reaction mixture was added with ethyl acetate and washed with saturated sodium hydrogencarbonate. The ethyl acetate layer was washed with water, dried over magnesium sulfate and evaporated under reduced pressure to give a residue, which was crystallized from a ether/n-hexane mixture to give 1.57 g of the objective compound in 55% yield.

m.p.: 191°-192° C.

Elementary Analysis (%) for C$_{20}$H$_{27}$NO$_5$.½H$_2$O

Calcd.: C,64.85; H,7.62; N,3.78
Found: C,65.14; H,7.47; N,3.81

NMR (CDCl₃) δ: 1.46(18H,s); 3.99(3H,s); 5.35(2H,d,J=2.6 Hz); 5.67(1H, s); 7.14(2H,s); 7.53(1H,t,J=2.6 Hz)

(3)
4-(3,5-di-tert-Butyl-4-hydroxybenzylidene)isoxazoldin-3-one

To a solution of 1.364 g (3.77 mmol) of the thus obtained methoxy carbonyl compound in methanol (136 ml) was added 7.54 ml of a solution of 1.0M sodium methoxide in methanol while being stirred vigorously at room temperature and the mixture was stirred for 5 minutes. To the reaction mixture were added dichloromethane and ice-water. The dichloromethane layer was washed with water, dried over magnesium sulfate and evaporated to give a residue, which was chromatographed on silica gel (n-hexane/ethyl acetate=2/1) to give 610 mg of the objective compound in 53% yield. A part of product was recrystallized from a dichloromethane/n-hexane mixture.
m.p.: 180°–183° C.

Elementary Analysis (%) for $C_{18}H_{25}NO_3 \cdot \frac{1}{2}H_2O$:

Calcd.: C,69.20; H,8.39; N,4.48
Found: C, 69.21: H, 8.17; N,4.44
NMR (CDCl₃) δ: 1.46(18H,s); 5.32(2H,d,J=2.6 Hz); 5.56(1H,brs.); 7.13(2H, s); 7.31(1H,t,J=2.6 Hz)

(4)
2-Carbamoyl-4-(3,5-di-tert-butyl-4-hydroxbenzylidene)isoxazolidin-3-one (Ie-1)

To a solution of 212 mg (0.7 mmol) of the thus obtained 4-(3,5-di-tert-butyl-4-hydroxybenzylidene)isoxazolidin-3-one in toluene (6 ml) was added 67 μl (0.77 mmol) of chlorosulfonyl isocyanate while being stirred with heating at 100° C. and allowed to react for 10 minutes. The reaction mixture was evaporated to give a residue, which was added with 4 ml of a acetic acid/water (2/1) mixture and stirred with heating at 100° C. for 10 minutes. The reaction mixture was evaporated to give a residue, which was dissolved in ethyl acetate. The reaction mixture was washed with water and saturated brine and evaporated under resuced pressure to give a residue, which was chromatographed on silica gel (n-hexane/ethyl acetate=2/1) to give 127 mg of the objective compound (Ie-1) in 52% yield. A part of product was recrystallized from a dichloromethane/n-hexane mixture.
m.p.: 178°–181° C.

Elementary Analysis (%) for $C_{19}H_{26}N_2O_4 3/4H_2O$:

Calcd.: C,63.40; H,7.70; N,7.78
Found: C,63.58; H,7.48; N,7.58
NMR (CDCl₃) δ: 1.47(18H,s); 5.37(2H,d,J=2.6 Hz); 5.69(1H,s); 7.15(2H,s); 7.49(1H,t,J=2.6 Hz)

EXAMPLE 33

(1)
1-Acetyl-3-(3,5-di-isopropyl-4-hydroxybenzylidene)-pyrrolidin-2-one

To a solution of 5.90 g (6 mmol) of (1-acetyl-2-oxopyrrolidin-3-yl)triphenylphosphonium bromide in ethanol (12 ml) were added 1.24 g (6 mmol) of 3,5-diisopropyl-4-hydroxybenzaldehyde and 1.67 ml (12 mmol) of triethylamine, and the mixture was stirred with heating at 60° C. for 2 hours. The reaction mixture was evaporated to give a residue, which was added with ethyl acetate and water. The ethyl acetate layer was washed with water, dried over magnesium sulfate and evaporated to give a residue, which was chromatographed on silica gel (toluene/ethyl acetate=4/1) to give 857 mg of the objective compound in 45% yield.

Elementary Analysis (%) for $C_{19}H_{25}NO_3$:

Calcd.: C,72.35; H,7.99; N,4.44
Found: C,72.40; H,8.07; N,4.49
NMR (CDCl₃) δ: 1.30(12H,d,J=7.0 Hz); 2.63(3H,s); 2.94–3.29(4H,m); 3.90 (2H,t,J=7.0 Hz); 7.25(2H,s); 7.52(1H,t,J=2.6 Hz)

(2)
3-(3,5-di-Isopropyl-4-hydroxybenzylidene)pyrrolidin-2-one

To a solution of 810 mg (2.57 mmol) of the thus obtained 1-acetyl-3-(3,5-di-isopropyl-4-hydroxybenzylidene)pyrrolidin-2-one in 5 ml of methanol and 10 ml of THF was added 2 ml of 1N aq. sodium hydroxide at room temperature and the mixture was stirred for 3 hours. the reaction mixture was poured into ice-water containing ethyl acecate and 3 ml of 1N hydrochloric acid. The ethyl acetate layer was washed with water and saturated brine, dried over magnesium sulfate and evaporated under reduced pressure to give a residue, which was crystallized from a ether/n-hexane mixture to give 800 mg of the objective compound as yellowish white crystal in 100% yield.
m.p.: 201°–202° C.

Elementary Analysis (%) for $C_{17}H_{23}NO_2 \frac{1}{4}H_2O$:

Calcd.: C,73.48; H,8.52; N,5.04
Found: C,73.43; H,8.44; N,5.00
NMR (CDCl₃) δ: 1.28(12H,d,J=6.8 Hz); 3.06–3.29(4H,m); 3.56(2H,t,J=6.8 Hz); 4.95–5.34(1H,-broad); 6.16–6.40(1H,broad); 7.22(2H,s); 7.22(2H,s); 7.33(1H,t,J=2.6 Hz)

(3)
1-(N-Hydroxy-N-methylcarbamoyl)-3-(3,5-di-isopropyl-4-hydroxybenzylidene)pyrrolidin-2-one (Ia-18)

Substantially in the same manner in Example 22, 273 mg (1 mmol) of the thus obtained 3-(3,5-di-isopropyl-4-hydroxybenzylidene)pyrrolidin-2-one was treated to give a residue, which was crystallized from a ether/n-hexane mixture to give 120 mg of the objective compound (Ia-18) in 35% yield.
m.p. 182°–183° C.

Elementary Analysis (%) for $C_{19}H_{26}N_2O_4$

Calcd.: C,65.88; H,7.56; N,8.09
Found: C,65.63; H,7.61; N,8.09
NMR (CDCl₃) δ: 1.29(12H,d,J=7.0 Hz); 3.03–3.25(4H,m); 3.34(3H,s); 3.97(2H,t,J=7.0 Hz); 7.24(2H,s); 7.49(1H,t,J=2.6 Hz); 9.70(1H,s)

EXAMPLE 34

1-Carbamoyl-3-(3-ethoxy-4-hydroxybenzylidene)pyrrolidin-2-one (Ia-19)

To a solution of 939 mg (2 mmol) of (1-carbamoyl-2-oxopyrrolidin-3-yl)triphenylphosphonium bromide in ethanol (16 ml) were added 332 mg (2 mmol) of 3-ethoxy-4-hydroxybenzaldehyde and 558 μl (4 mmol) of triethylamine, and the mixture was stirred at 60° C. for 2 hours. The reaction mixture was evaporated to give a residue, which was dissolved in diisopropyl ether and treated with 4 ml of 1N aq. sodium hydroxide. The aqueous layer was made acid with 1N hydrochloric acid under ice-cooling and the product was dissolved in ethyl acetate, washed with water and saturated brine, dried over magnesium sulfate and evaporated to give a residue, which was crystallized from a dichloromethane/n-hexane mixture to give 143 mg of the objective compound (Ia-19) in 26% yield.

m.p.: 204°–205° C.

Elementary Analysis (%) for $C_{14}H_{16}N_2O_4$:

Calcd.: C,60.86; H,5.84; N,10.14
Found: C,60.76; H,5.91; N,10.10

NMR (CDCl$_3$) δ: 1.49(3H,t,J=7.8 Hz); 3.06(2H,dt,J=7.4 & 2.8 Hz); 3.95(2H,t,J=7.4 Hz); 4.16 (2H,q,J=7.0 Hz); 5.20(1H,brs); 5.96(1H,s); 6.96–7.26(3H,m), 7.43(1H,t,J=2.8 Hz); 8.52(1H,brs)

EXAMPLE 35

(1)

1-(N-tert-Butyldimethylsilyloxy-N-methylcarbamoyl)-pyrrolidin-2-one

To a chilled solution (−70° C.) of 2 g (23.5 mmol) of 2-oxopyrrolidine in 10 ml of THF was added 24 ml of a THF solution of 1.0M lithium bis-(trimethylsilyl)amide under a nitrogen atmosphere. Then 6.62 g of N-hydroxy-N-methylcarbamate-O-tert-butyldimethylsilyl ether was added thereto and the mixture was stirred at room temperature for 3 hours. The reaction mixture was poured into ethyl acetate and the mixture was washed with 0.1N hydrochloric acid, water, and saturated brine and dried over magnesium sulfate and evaporated to give a residue, which was chromatographed on silica gel (toluene/ethyl acetate=10/1) to give the objective compound as colorless oil in 70% yield.

NMR (CDCl$_3$) δ: 0.21(6H,s); 0.97(9H,s); 2.08(2H,quinted,J=7.6 Hz); 2.49 (2H,t,J=7.9); 3.24 (3H,s); 3.76(2H,t,J=7.6 Hz); 2.49 (2H,t,J=7.9); 3.24 (3H,s); 3.76(2H,t,J=7.0 Hz)

(2)

1-(N-Hydroxy-N-methylcarbamoyl)-3-(3,5-di-tert-butyl-4-hydroxybenzoyl)pyrrolidin-2-one (Ia-20)

To a chilled solution (−78° C.) of 2 g (7.34 mmol) of the thus obtained 1-(N-tert-butyldimethylsilyloxy-N-methylcarbamoyl)pyrrolidin-2-one in THF (5 ml) was added 8.1 ml (8.1 mmol) of a THF solution of 1.0M lithium bis(trimethylsilyl)amide under a nitrogen atmosphere, and the mixture was stirred for 1 hour. To the reaction mixture was dropwise added 5 ml of a THF solution of 1.55 g (5 mmol) of methyl-3,5-di-tert-butyl-4-methoxymethyloxybenzoate while being stirred at room temperature for 20 hours. The reaction mixture was poured into ethyl acetate, washed with 0.1N hydrochloric acid and saturated brine, dried over magnesium sulfate and evaporated to give a residue, which was dissolved in 12 ml of acetone and added with 0.6 ml of conc. hydrochloric acid. The reaction mixture was stirred at room temperature for 20 hours, and poured into ethyl acetate, washed with water and saturated brine, dried over magnesium sulfate and evaporated to give a residue, which was chromatographed on silica gel (toluene/ethyl acetate=10/1) to give 200 mg of the objective compound (Ia-20) as white amorphous in 10% yield.

Elementary Analysis (%) for $C_{21}H_{30}N_2O_5$:

Calcd.: C,64.60; H,7.74; N,7.17.

Found: C,64.77; H,7.75; N,6.93.

IR (KBr) cm$^{-1}$: 3560, 2955, 1700–1662.

NMR (CDCl$_3$) δ: 1.48(18H,s); 2.27–2.45(1H,m); 2.63–2.80(1H,m); 3.27(3H,s); 3.85–4.09(2H,m); 4.62(1H,d.d.,J=6.4,8.9 Hz); 5.86(1H,s); 7.94(2H,s); 8.87(1H,s).

EXAMPLE 36

(1)

1-(N-Benzyloxycarbamoyl)-3-bromopyrrolidin-2-one

A solution of 3.28 g (20 mmol) of 3-bromopyrrolidin-2-one and 5.346 g (22 mmol) of N-benzyloxyphenylcarbamate (J. Org. Chem., 21, 660, (1956)) in 20 ml of pyridine was refluxed for 12 hours. The reaction mixture was evaporated to give a residue, which was dissolved in ethyl acetate. The ethyl acetate layer was washed with 1N hydrochloric acid, water and saturated brine under ice-cooling, dried over magnesium sulfate and evaporated to give a residue, which was chromatographed on silica gel (toluene/ethyl acetate=2/1) and recrystallized from a dichloromethane/n-hexane mixture to give 3.62 g of the objective compound in 60% yield.

m.p.: 137°–142° C.

IR (KBr) cm$^{-1}$: 3272, 1719, 1694.

NMR (CDCl$_3$) δ: 2.29–2.41 (1H, m); 2.54–2.71 (1H, m); 3.91–3.97 (2H, m); 4.46–4.51 (1H, m); 4.96 (2H, s); 7.35–7.44 (5H, m); 10.43 (1H, s).

(2)

{1-(N-Benzyloxycarbamoyl)-2-oxopyrrolidin-3-yl}triphenylphosphonium bromide

To a solution of 2.222 g (7.1 mmol) of the thus obtained 1-(N-benzyloxycarbamoyl)-3-bromopyrrolidin-2-one in 50 ml of tetrahydrofuran was added 1.862 g (7.1 mmol) of triphenylphosphine, and the mixture was stirred at 80° C. for 24 hours. The reaction mixture was cooled with ice to deposit crystals, which were filtered off with cooled tetrahydrofuran, to give 3.177 g of the objective compound in 83% yield.

m.p.: 235°–238° C.

IR (KBr) cm$^{-1}$: 3400, 3302, 1717, 1584.

NMR (CDCl$_3$) δ: 1.99–2.29 (1H, m); 3.05–3.24 (1H, m); 3.76–3.84 (1H, m); 4.08–4.22 (1H, m); 4.85 (2H, q, J=10.6 Hz); 7.35 (5H, s); 7.59–8.00 (16H, m); 10.10 (1H, s).

(3)

1-(N-Benzyloxycarbamoyl)-3-(3,5-di-methoxy-4-hydroxybenzylidene)pyrrolidin-2-one To a solution of 2.88 g (5 mmol) of the thus obtained wittig base in 99% ethanol (30 ml) were added 911 mg (5 mmol) of 3,5-di-methoxy-hydroxybenzaldehyde and 1.4 ml (10 mmol) of triethylamine, and the mixture was stirred at 70° C. for 1.0 hour. The reaction mixture was evaporated to give a residue, which was crystallized from a ethanol/n-hexane (=1/1) mixture to give 1.90 g of the objective compound in 85% yield.

m.p.: 167°–170° C.

NMR (CDCl$_3$) δ: 3.11 (2H, dt, J=7.4,2.8Hz); 3.93 (6H, s); 3.97 (2H, t, J=7.4 Hz); 5.00 (2H, s); 5.83 (1H, s); 6.74 (2H, s); 7.32–7.51 (6H, m); 10.87 (1H, s).

(4)
1-(N-Hydroxycarbamoyl)-3-(3,5-di-methoxy-4-hydroxybenzylidene)pyrrolidin-2-one (Ia-21)

To a solution of 800 mg (2 mmol) of 1-(N-benzyloxycarbamoyl)-3-(3,5-di-methoxy-4-hydroxybenzylidene)pyrrolidin-2-one in a mixture of anisole (12 ml) and nitromethane (12 ml) was added a solution of 1.6 g (12 mmol) of aluminium chloride in anisole (4 ml) under a nitrogen atmosphere while being stirred under ice-cooling and the mixture was stirred at room temperature for 2 hours. The reaction mixture was poured into 6 ml of cooled 2N hydrochloric acid and the mixture was stirred for 1 hour and extracted with ethyl acetate. The ethyl acetate layer was washed with saturated brine, dried over magnesium sulfate and evaporated to give a residue, which was recrystallized from a methylene chloride/ether mixture to give 387 mg of the objective compound in 63% yield.

m.p.: 203°–204° C.

NMR (DMSO-d$_6$) δ: 3.05–3.17 (2H, m); 3.72–3.88 (2H, m); 3.81 (6H, s); 6.90 (2H, s); 7.25–7.32 (1H, m); 8.96–9.28 (2H, broad); 10.44 (1H, broad, s).

EXAMPLE 37

1-Carbamoyl-3-(3,5-dimethyl-4-hydroxybenzylidene)-pyrrolidin-2-one (Ia-22)

2.46 g (5.24 mmol) of (1-carbamoyl-2-oxopyrrolidin-3-yl)triphenylphosphonium bromide (obtained from the reaction of 1-carbamoyl-3-bromopyrrolidin-2-one prepared in the same manner as in Example 1 (1) with triphenylphosphine), 787 mg (5.2 mmol) of 3,5-dimethyl-4-hydroxybenzaldehyde, and 1.1 g (10.08 mmol) of triethylamine were dissolved in 50 ml of ethanol and the solution was stirred at 80° C. for 3 hours. After cooled down, the deposited crystals were filtered off and the filtrate was recrystallized from a ethyl acetate/n-hexane mixture to give 420 mg of the objective compound in 31% yield.

m.p.: 239.5°–241.5° C.

Elementary Analysis (%) for C$_{14}$H$_{16}$N$_2$O$_3$

Calcd.: C,64.60; H,6.20; N,10.76.
Found: C,64.56; H,6.22; N,10.70.
IR (KBr) cm$^{-1}$: 3450, 1705, 1682.

NMR (d$_6$-DMSO) δ: 2.20 (6H, s); 2.99 (2H, dt, J=3,7 Hz); 3.76 (2H, t, J=7 Hz); 7.19 (3H, broad); 7.41 (1H, broad); 8.06 (1H, broad); 8.85 (1H, broad).

EXAMPLE 38

(1)
1-Acetyl-3-(4-acetoxy-3,5-di-tert-butylbenzylidene)pyrrolidin-2-one

To a solution of 450 mg (1.5 mmol) of 3-(3,5-di-tert-butyl-4-hydroxybenzylidene)pyrrolidin-2-one in 10 ml of acetic anhydride was added 0.3 ml of conc. sulfuric acid and heated at 170° C. for 3 hours. The reaction mixture was evaporated under reduced pressure to give a residue, which was powdered with a ether/n-hexane mixture to give 505 mg of the objective crude compound as brown powder. This was employed for the subsequent reaction without purification.

NMR (CDCl$_3$) δ: 1.37 (18H, s); 2.37 (3H, s); 2.63 (3H, s); 3.05 (2H, dt, J=7.6,2.8 Hz); 3.89 (2H, t, J=7.6 Hz); 7.49 (2H, s); 7.54 (1H, t, J=2.8 Hz).

(2)
3-(4-Acetoxy-3,5-di-tert-butylbenzylidene)pyrrolidin-2-one

To a solution of 386 mg (1 mmol) of the thus obtained crude compound in 40 ml of methanol and 20 ml of tetrahydrofuran was added 0.1 ml (0.1 mmol) of a methanol of 1 m/L sodium methoxide while being stirred under ice-cooling and the reaction mixture was stirred at room temperature for 1 hour and poured into ice-water containing ethyl acetate and 1 ml of 1N hydrochloric acid. The ethyl acetate layer was washed with saturated brine, dried over magnesium sulfate and evaporated under reduced pressure to give 345 mg of the objective crude compound as foam. This compound was employed for the subsequent reaction without purification.

NMR (CDCl$_3$) δ: 1.36 (18H, s); 2.37 (3H, s); 3.18 (2H, dd, J=6.4,2.8 Hz); 3.59 (2H, t, J=6.4 Hz); 6.23 (1H, brs); 7.37 (1H, t, J=2.8 Hz); 7.48 (2H, s).

(3)
1-(N-Hydroxy-N-methylcarbamoyl)-3-(4-acetoxy-3,5-di-tert-butylbenzylidene)pyrrolidin-2-one (Ia-23)

Substantially in the same manner as in Example 11, 226 mg (0.66 mml) of the thus obtained crude compound and 222 mg (0.79 mmol) of N-hydroxy-N-methylphenylcarbamate-O-tert-butyldimethylsilyl ether were treated and crystallized from a methylene chloride/hexane mixture to give 66 mg of the objective compound (Ia-23) in 56% yield.

m.p.: 176°–177° C.

NMR (CDCl$_3$) δ: 1.37 (18H, s); 2.37 (3H, s); 3.13 (2H, dt, J=7.4,2.8 Hz); 3.35 (3H, s); 3.98 (2H, t, J=7.4 Hz); 7.47 (2H, s); 7.51 (1H, t, J=2.8 Hz); 9.57 (1H, s).

EXAMPLE 39

(1)
1-(N-tert-Butoxycarbonylaminocarbamoyl)-3-bromopyrrolidin-2-one

A mixture of 4.1 g (25 mmol) of 3-bromopyrrolidin-2-one and 6.94 g (27.5 mmol) of tert-butylphenylhydrazine dicarboxylate in 50 ml of pyridine was refluxed for 10 hours. The reaction mixture was evaporated to give a residue, which was dissolved in acetic acid under ice-cooling, washed with 1N hydrochloric acid, water and saturated brine and dried over magnesium sulfate and evaporated. The obtained residue was chromatographed on silica gel (n-hexane/ethyl acetate=1/1) and crystallized from a siopropyl ether/dichloromethane mixture to give 4.429 g of the objective compound as white crystal in 55% yield.

m.p.: 122°–123° C.

NMR (CDCl$_3$) δ: 1.49 (9H, s); 2.26–2.44 (1H, m); 2.54–2.73 (1H, m); 3.95–4.00 (2H, m); 4.53 (1H, dd, J=7.2,3.4 Hz); 6.29 (1H, broad s); 9.56 (1H, broad s).

(2)
{1-(N-tert-Butoxycarbonylhydrazinocarbonyl)-2-oxopyrrolidin-3-yl}triphenylphosphonium bromide To 3.88 g (12.04 mmol) of the thus obtained 1-(N-tert-butoxycarbonylaminocarbamoyl)-3-bromopyrrolidin-2-one and 3.157 g (12.04 mmol) of triphenylphosphine was added 7 ml of tetrahydrofuran and the mixture was heated at 90° C. for 7 hours to give a compound as wax, which was washed with tetrahydrofuran to give 4.077 g of the objective crude compound as waxy residue.

(3)
1-(N-tert-Butoxycarbonylhydrazinocarbonyl)-3-(3,5-di-tert-butyl-4-hydroxybenzylidene)pyrrolidin-2-one (Ia-24)

To a solution of 4.077 g of the thus obtained crude wittig base in 80 ml of absolute ethanol were added 1.64 g (7.0 mmol) of 3,5-di-tert-butyl-4-hydroxybenzaldehyde and 1.95 ml (14 mmol) of triethylamine and the mixture was heated at 70° C. for 3 hours. The reaction mixture was evaporated to give a residue, which was added with ethyl acetate and water and the mixture was stirred. The ethyl acetate layer was washed with water, dried over magnesium sulfate and evaporated under reduced pressure to give a residue, which was recrystallized from a dichloromethane/diisopropyl ether mixture to give 515 mg of the objective compound (Ia-24) as white crystal in 9.3% yield. Then the mother liquor was chromatographed on silica gel (n-hexane/ethyl acetate=4/1) and recrystallized from a dichloromethane/diisopropyl ether mixture to give 607 mg of the objective compound as white crystal in 11.0% yield.

m.p.: 228°–229° C.

NMR (CDCl$_3$) δ: 1.47 (18H, s); 1.49 (9H, s); 3.08 (2H, dt, J=6.8, 2.6 Hz); 3.95 (2H, t, J=6.8 Hz); 5.58 (1H, s); 6.35 (1H, broad s); 7.37 (2H, s); 7.48 (1H, t, J=2.6 Hz); 10.04 (1H, broad s).

EXAMPLE 40

1-(N-Hydrazinocarbonyl)-3-(3,5-di-tert-butyl-4-hydroxybenzylidene)pyrrolidin-2-one (Ia-25)

To a solution of 2.023 g (4.40 mmol) of the compound (Ia-24) obtained in Example 39 in 20 ml of dichloromethane was added 5 ml of trifluoroacetic acid under ice-cooling. The reaction mixture was stirred at room temperature for 3 hours and evaporated under reduced pressure to give a residue, which was dissolved in ethyl acetate, washed with water, dried over magnesium sulfate and evaporated under reduced pressure. The obtained residue was chromatographed on silica gel (n-hexane/ethyl acetate=1/1) and crystallized from a ethyl acetate/n-hexane mixture to give 1.15 g of the objective compound as white crystal in 73% yield.

m.p.: 225°–226° C.

NMR (CDCL$_3$) δ: 1.44 (18H, s); 3.09 (2H, dt, J=6.8, 2.6 Hz); 3.95 (2H, t, J=6.8 Hz); 5.57 (1H, s); 7.37 (2H, s); 7.46 (1H, t, J=2.6 Hz); 9.57 (1H, s).

EXAMPLE 41

(1)
3-Bromo-1-(N-dimethylaminocarbamoyl)pyrrolidin-2-one

Substantially in the same manner as in Example 39 (1), 8.2 g (50 mmol) of 3-bromopyrrolidin-2-one and 9.91 g (55 mmol) of N-dimethylaminophenylcarbamate in 100 ml of pyridine were treated to give 7.96 g of the objective compound as white crystal in 63.6% yield.

m.p.: 78°–79° C.

NMR (CDCl$_3$) δ: 2.26–2.44 (1H, m); 2.50–2.68 (1H, m); 2.66 (6H, s); 3.90 –4.00 (2H, m); 4.53 (1H, dd, J=10.6, 3.6 Hz); 9.04 (1H, s).

(2)
{1-(N-Dimethylaminocarbamoyl)-2-oxopyrrolidin-3-yl}phosphonium bromide

Substantially in the same manner as in Example 39 (2), 4.25 g (17 mmol) of the thus obtained 3-bromo-1-(N-dimethylaminocarbamoyl)-pyrrolidin-2-one and 4.46 g (17 mmol) of triphenylphosphine were treated to give 8.31 g of the objective crude compound as waxy residue.

(3)
1-(N-Dimethylaminocarbamoyl)-3-(3,5-di-tert-butyl-4-hydroxybenzylidene)pyrrolidin-2-one (Ia-26)

Substantially in the same manner as in Example 39 (3), 8.31 g of the thus obtained {1-(N-dimethylaminocarbamoyl)-2-oxopyrrolidin-3-yl-phosphonium bromide, 3.79 g (16.2 mmol) of 3,5-di-tert-butyl-4-hydroxybenzaldehyde and 4.51 ml (32.4 mmol) of triethylamine were treated to give 2.91 g of the objective compound (Ia-26) in 46.4% yield.

m.p.: 133°–134° C.

NMR (CDCl$_3$) δ: 1.47 (18H, s); 2.70 (6H, s); 3.04 (2H, d.t., J=6.8, 2.8 Hz); 3.96 (2H, t, J=6.8 Hz); 5.56 (1H, s); 7.36 (2H, s); 7.43 (1H, t, J=2.8 Hz); 9.58 (1H, s).

EXAMPLE 42

(1)
3-Bromo-1-{N-(4-morpholino)carbamoyl}pyrrolidin-2-one

Substantially in the same manner as in Example 39 (1), 8.2 g (50 mmol) of 3-bromopyrrolidin-2-one and 12.22 g (55 mmol) of N-morpholinophenylcarbamate in 100 ml of pyridine were treated to give 6.72 g of the objective compound as white crystal in 46% yield.

m.p.: 118°–119° C.

NMR (CDCl$_3$) δ: 2.27–2.42 (1H, m); 2.52–2.73 (1H, m); 2.92 (4H, t, J=4.8 Hz); 3.83 (4H, t, J=4.8 Hz); 3.90–3.99 (2H, m); 4.54 (1H, dd, J=7, 3.4 Hz); 9.16 (1H, s).

(2)
[1-{N-(4-Morpholino)carbamoyl}-2-oxopyrrolidin-3-yl]phosphonium bromide

Substantially in the same manner as in Example 39 (2), 4.09 g (14 mmol) of the thus obtained 3-bromo-1-{N-(4-morpholino)carbamoyl}pyrrolidin-2-one and 3.67 g (14 mmol) of triphenylphosphine were treated to give 7.46 g of the objective crude compound as waxy residue.

(3)
1-{N-(4-Morpholino)carbamoyl}-3-(3,5-di-tert-butyl-4-hydroxybenzylidene)pyrrolidin-2-one (Ia-27)

Substantially in the same manner as in Example 39 (3), 7.46 g of the thus obtained [1-{N-(4-morpholino)carbamoyl}-2-oxopyrrolidin-3-yl]-phosphonium bromide, 3.16 g (13.5 mmol) of 3,5-di-tert-butyl-4-hydroxybenzaldehyde and 3.76 ml (27 mmol) of triethylamine were treated to give 5.96 g of the objective compound as white crystal in 99% yield.

m.p.: 195°–196° C.

NMR (CDCl$_3$) δ: 1.47 (18H, s); 2.96 (4H, t, J=4.8 Hz); 3.05 (2H, d.t., J=6.6H, 2.8 Hz); 3.85 (4H, t, J=4.8 Hz); 3.95 (2H, t, J=6.6 Hz); 5.76 (1H, s); 7.37 (2H, s); 7.44 (1H, t, J=2.8 Hz); 9.70 (1H, s).

Physical constants of the compounds Ia-1-9, Ib-1-3 and Ic-1-3 obtained in Example 1–15 are shown in the following Table 1 No. 1–No. 5.

TABLE 1

| Compd. No. | m.p. (°C.) | $IR_{84}$ max (cm$^{-1}$) | NMR δ ppm | Elementary Analysis Calcd. (%) Found (%) |
|---|---|---|---|---|
| Ia-1 | 134~136 | (KBr) 3600, 3540(OH), 3388(NH), 2950(CH), 1706(CO), | (CDCl$_3$) 1.47(18H, s), 3.06(2H, d. t, J=3, 7Hz), 3.95(2H, t, J=7Hz), 5.20~5.35(1H, broad), 5.57(1H, s), 7.38(2H, s), 7.48(1H, t, J=3Hz), 8.48~8.65(1H, broad). | (C$_{20}$H$_{28}$N$_2$O$_3$) C, 69.74; H, 8.19; N, 8.13; C, 69.35; H, 8.26; N, 7.96. |
| Ia-2 | 200~201 | (KBr) 3570, 3330, 1710, 1638, 1547. | (CDCl$_3$) 1.47(18H, s), 2.95(3H, d. t, J=4.8Hz), 3.04(2H, dt, J=2.8, 7.1Hz), 3.95(2H, t, J=7.1Hz), 5.54 (1H, s), 7.37(2H, s), 7.44(1H, t, J=3Hz), 8.50~8.70(1H, broad). | (C$_{21}$H$_{30}$N$_2$O$_3$) C, 70.36; H, 8.44; N, 7.81; C, 70.54; H, 8.47; N, 7.78. |
| Ia-3 | 180.5~183 | (KBr) 3430, 2960, 1712, 1659. | (CDCl$_3$) 1.47(18H, s), 3.05(6H, s), 3.09(2H, d, t, J=2.6, 7.1Hz), 3.89 (2H, t, J=7.1Hz), 5.51(1H, s), 7.36 (2H, s), 7.40(1H, t, J=2.6Hz). | (C$_{22}$H$_{32}$N$_2$O$_3$) C, 70.94; H, 8.66; N, 7.52; C, 70.89; H, 8.57; N, 7.40. |
| Ia-4 | 202~205 | (KBr) 3630, 3600, 3400, 3240 2950, 1700 1639. | (CDCl$_3$) 1.46(18H, s), 3.09(2H, d. t, J=2.2, 7.0Hz), 3.95(2H, t, J=7.0 Hz), 5.58(1H, s), 7.37(2H, s), 7.46(1H, t, J=2.2Hz). | (C$_{20}$H$_{28}$N$_2$O$_4$) C, 66.64; H, 7.83; N, 7.77; C, 66.52; H, 7.89; N, 7.76. |
| Ia-5 | 187.5~188.5 | (KBr) 3620, 3270, 2970, 1706, | (CDCl$_3$) 1.47(18H, s), 3.09(2H, d. t, J=2.4, 7.3Hz), 3.85(3H, s), 3.95 (2H, t, J=7.3Hz), 5.59(1H, s), 7.37 (2H, s), 7.45(1H, t, J=2.4Hz), 10.97(1H, s). | (C$_{21}$H$_{30}$N$_2$O$_4$·0.1H$_2$O) C, 67.03; H, 8.09; N, 7.44; C, 66.95; H, 8.05; N, 7.47. |
| Ia-6 | 164~166 | (KBr) 3565, 2960, 1682, 1655, 1630. | (CDCl$_3$) 1.47(18H, s), 3.13(2H, d. t, J=2.4, 7.3Hz), 3.34(3H, s), 3.98 (2H, t, J=7.3Hz), 5.59(1H, s), 7.37 (2H, s), 7.49(1H, t, J=2.4Hz). | (C$_{21}$H$_{30}$N$_4$O$_4$) C, 67.36; H, 8.07; N, 7.48; C, 67.41; H, 8.18; N, 7.35. |
| Ia-7 | 130~132 | (KBr) 3510, 2960, 1712, 1688, 1636. | (CDCl$_3$) 1.48(18H, s), 3.10(2H, d. t, J=2.6, 6.8Hz), 3.29(3H, s), 3.82 (3H, s), 3.88(2H, t, J=6.8Hz), 5.54 (1H, s), 7.37(2H, s), 7.45(1H, t, J=2.6Hz). | (C$_{22}$H$_{32}$O$_2$O$_4$) C, 68.01; H, 8.30; N, 7.21; C, 68.01; H, 8.30; N, 7.21. |
| Ia-8 | 168~169 | (KBr) 3598, 2960, 1670, 1625. | (CDCl$_3$) 1.30(3H, t, J=7.2Hz), 1.47 (18H, s), 3.12(2H, d, t, J=2.6, 7.1Hz), 3.74(2H, q, J=7.2Hz), 3.98 (2H, t, J=7.1Hz), 5.58(1H, s), 7.37 (2H, s), 7.48(1H, t, J=2.6Hz), 9.62 (1H, s). | (C$_{22}$H$_{32}$N$_2$O$_4$) C, 68.01; H, 8.30; N, 7.21; C, 67.73; H, 8.14; N, 7.13. |
| Ia-9 | 179~180 | (KBr) 3590, 3430, 1676, 1661, 1625, 1592. | (CDCl$_3$) 1.30(6H, d, J=6.6Hz), 1.47 (18H, s), 3.11(2H, d.t, J=2.6, 7.0 Hz), 3.97(2H, t, J=7.4Hz), 4.56(1H sept., J=6.6Hz), 5.56(1H, s), 7.37 (2H, s), 7.45(1H, t, J=2.6Hz), 9.30 (1H, s). | (C$_{23}$H$_{34}$N$_2$O$_4$) C, 68.63; H, 8.51; N, 6.96; C, 68.46; H, 8.69; N, 6.83. |
| Ib-1 | 181~185 | (KBr) 3614, 3356, 3188, 1719, 1679. | (CDCl$_3$) 1.48(18H, s), 5.00(2H, s), 5.42(b.s, NH), 5.56(s, OH), 7.42 (2H, s), 7.57(1H, s), 8.66(b.s, NH). | (C$_{19}$H$_{26}$N$_2$O$_3$S) C, 62.95; H, 7.23; N, 7.73; S, 8.85; C, 62.91; H, 7.15; N, 7.80; S, 8.69. |
| Ib-2 | 192~197 | (KBr) 3612, 3342, 3226, 1691, | (CDCl$_3$) 1.47(18H, s), 4.98(2H, s), 5.57(1H. s), 7.40(2H, s), 7.56(1H, s). | (C$_{19}$H$_{26}$N$_2$O$_4$S) C, 60.29; H, 6.92; N, 7.40; S, 8.47; |

TABLE 1-continued

| Compd. No. | m.p. (°C.) | IR$_{84}$ max (cm$^{-1}$) | NMR δ ppm | Elementary Analysis Calcd. (%) Found (%) |
|---|---|---|---|---|
| | | 1590. | | C, 60.01; H, 6.85; N, 7.29; S, 8.08. |
| Ib-3 | 145~147 | (KBr) 3618, 3350, 1681, 1600. | (CDCl$_3$) 1.48(18H, s), 3.37(3H, s), 5.00(2H, s), 5.57(1H, s), 7.26(2H, s), 7.58(1H, s), 9.11(1H, s), | (C$_{20}$H$_{28}$N$_2$O$_4$S) C, 61.20; H, 7.19; N, 7.14; S, 8.17; C, 60,85; H, 7.36; N, 7.09; S, 8.06. |
| Ic-1 | 173~176 | (KBr) 3614, 3378, 3208, 1743, 1698, 1664. | (CDCl$_3$) 1.46(18H, s), 5.26(1H, b. s), 5.46(1H, s), 5.75(2H, s), 6.41 (s, 1H), 7.55(2H, s), 8.02(1H, b. s). | (C$_{19}$H$_{26}$N$_2$O$_4$) C, 65.87; H, 7.57; N, 8.09; C, 65.61; H, 7.94; N, 7.47. |
| Ic-2 | 203.5~205 | (KBr) 3624, 3326, 3268, 1728, 1674. | (CDCl$_3$) 1.45(18H, s), 5.48(1H, s), 5.75(2H, s), 6.42(1H, s), 6.58(1H, b.s), 7.54(2H, s), 10.29(1H, s). | (C$_{19}$H$_{26}$N$_2$O$_5$) C, 62.96; H, 7.23; N, 7.73; C, 62.81; H, 7.36; N, 7.56. |
| Ic-3 | | (CHCl$_3$) 3624, 3300(b), 1700, 1592. | (CDCl$_3$) 1.46(18H, s), 3.31(3H, s), 5.47(1H, s), 5.78(2H, s), 6.44(1H, s), 7.55(2H, s), 9.39(1H, s). | |

Experimental Examples are set forth to show that the compounds of the present invention are useful for anti-inflammatory agent.

EXPERIMENTAL EXAMPLE 1

Inhibitory Activity on PGE$_2$ Production from Rat Synovia Cells

LEW/Crj rats (male, 300-350 g weight) were subjected to synovectomy. The isolated synovia cells were subcultivated under a certain condition up to a well amount of cells for the experiment. The cells were dispensed to each well of a 96-well microtiter plate at a concentration of 4×10$^3$/160 μl/well and then cultivated for 72 hours in a CO$_2$ incubator. Serial dilutions (20 μl each) of a test compound and human IL-1 β(final concentration: 30 U/ml) were added to the wells and incubated for 15 hours in a Co$_2$ incubator. After the incubation, the supernatant was collected from each well and stored at −80° C. until PGE$_2$ assay. After thawed, PGE$_2$ in each supernatant was determined by RIA using $^{125}$I—PGE$_2$. The results are shown on Table 2.

EXPERIMENTAL EXAMPLE 2

Inhibitory Activity on LTB$_4$ Production from Rat Peritoneal Cells

To each male Jcl-SD rat (300-350 g weight) was intraperitoneally administered 10 ml of Hanks' solution containing 0.1% bovine serum albumin (hereinafter referred to as BSA) and 25 U/ml of heparin. Then the ascites were collected and centrifuged (1500 rpm×5 min., at 4° C.). The resulting cell fraction (precipitation) was suspended and adjusted at 1×10$^5$ cells/ml with Hanks' solution containing 0.1% BSA. The thus obtained suspension (800 μl, 8×10$^5$ cells) was dispensed into polypropylene tubes and incubated at 37° C. 10 min, and successively for 10 min. after addition of serial dilutions (100 μl each) of a test sample. Next, 100 μl of Ca-ionophore A23187 (final concentration: 1 μM) was added to the resulting suspension and allowed to stand for 15 min, then the mixture was ice-cooled to terminate the reaction. The reaction mixtures were centrifuged (3000 rpm×5 min., at 4° C.) to give supernatants, which were collected and stored at −80° C. until LTB$_4$ assay. After thawed, the LTB$_4$ assay was performed by RIA using $^3$H—LTB$_4$. The results are shown on Table 2.

EXPERIMENTAL EXAMPLE 3

Inhibitory Activity on IL-1 Production caused by The Stimulation of LPS in THP-1 Cells A suspension of THP-1 cells in RPMI 1640 solution (5×10$^5$ cells/ml) was dispensed to each well of a 24-well microtiter plate at 800 μl/well. Serial dilutions (100 μl each) of a test compound and LPS (final concentration: 10 μg/ml) were further added to each well and the plate was kept at 37° C. for 24 hours. Then, the supernatant was collected from each well and centrifuged (3000 rpm×10 min.). The IL-1 assay was performed by RIA using $^{125}$I—IL-1 β. The results are shown on Table 2.

EXPERIMENTAL EXAMPLE 4

Inhibitory Activity on Carrageenin-Induced Paw-Edema of Rat

This test was performed by partially modifying the Winter et al's method (Winter, C. A. et al., Proc. Soc. Exp. Biol. Med., 111, P54, 1962). Namely, male LEW/Crj rats (6-week-old, 140-170 g weight) fasted for 24 hours were used (7 to 8 rats per group).

A solution (0.1 ml) containing 1% λ-carrageenin (PICININ-A, Zushikagaku) was injected into the subplantar tissue of the right hind paw of each rat orally administered a test compound before 1 hour, to induce edema. The paw volume was calculated plethysmographically before and after the injection at an interval of 1 hour until 5 hours later. The inhibitory rate of the drug-administered group was calculated, with the vehicle group as the reference, to determine the efficacy of the test compounds by Dunnett-t assay. The anti-edema activity was indicated as ED$_{30}$ calculated, by regression analysis method, based on the inhibitory rate shown 3 or 4 hours later after the administration of carrageenin. The results are shown on Table 2.

(Reference compound: N-methoxy-3-(3,5-di-tert-butyl-4-hydroxybenzylidene)-2-pyrrolidone (described in Kokai 61-257967))

TABLE 2

| Compound No. | IC$_{50}$ (μM) | | | ED$_{30}$ (mg/Kg) Inhibitory Activities to Carrageenin-Induced Paw Edema of Rat |
|---|---|---|---|---|
| | Rat SVC PGE$_2$ | Rat PEC LTB$_4$ | THP-1 IL-1 | |
| Ia-1 | 0.4 | 4 | 20 | 18 |
| Ia-4 | 0.2 | 3 | 25 | 16 |
| Ia-6 | 0.009 | 3 | 34 | 9 |
| Reference Compound | 0.005 | 6 | >100 | 3 |

Experimental Example 5

Inducing Activities on Injury at Tunica Mucosa of Rat

Sixs LEW/Crj male rats (six week old, 140–160 g weight) were used per one group. A drug was orally administered to each rat fasted for 24 hours, then six hours later each rat were bled to death under anesthesia of ether. From each rat was taken out the stomach, in which about 6 ml of physiological saline was filled, then the stomach was steeped in 1% formalin solution for 15 min. The stomach was incised along with curvatura ventriculi major and observed with an actual-microscope to see the injured condition thereof, then the number of rats injuried at stomach and the length of hemorrhage macula were determined. The degree of the injury was shown as Lesion index (mm) which was the cumulative value of the length of hemorrhage macula in each administered group. The results are shown on Table 3. (Reference Compound: N-methoxy-3-(3,5-ditert-butyl-4-hydroxybenzyliden)-2-pyrrolidone (described in Kokai 61-257967))

TABLE 3

| Comd. No. | Dosage mg/kg | Injury at Tunica Mucosa Ventriculi | |
|---|---|---|---|
| | | Number Occurrence/Sample | Degree of Injury (mm) |
| Ia-1 | 10 | 0/6 | 0 ± 0 |
| | 100 | 0/6 | 0 ± 0 |
| | 200 | 0/6 | 0 ± 0 |
| Ia-4 | 100 | 0/8 | 0 ± 0 |
| | 200 | 0/8 | 0 ± 0 |
| | 400 | 3/8 | 0.2 ± 0.1 |
| Ia-6 | 10 | 0/6 | 0 ± 0 |
| | 30 | 3/6 | 0.6 ± 0.5 |
| | 100 | 3/6 | 1.0 ± 0.5 |
| Ref. Comd. | 3 | 6/6 | 4.5 ± 1.3 |
| | 10 | 6/6 | 7.2 ± 1.2 |
| | 30 | 6/6 | 11.2 ± 2.2 |

As revealed from the above experimental results, the compounds of the present invention may be applied to an advantage anti-inflammatory agent which hardly causes stomach disease which has been the representative side effect caused by prior anti-inflammatory agents.

We claim:

1. A compound represented by the formula:

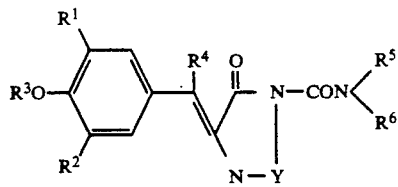

wherein R$^1$ and R$^2$ each is independently hydrogen, alkyl, alkoxy, or halogen; R$^3$ is hydrogen or, aromatic or aliphatic acyl; R$^4$ is hydrogen, alkyl, hydroxy, alkoxy, cyano, or halogen; R$^5$ and R$^6$ each is independently hydrogen, alkyl, aryl, aralkyl, amino which is unsubstituted or substituted by alkyl, hydroxy, alkoxy, aromatic or aliphatic acyl, or alkoxycarbonyl, or OR$^7$ wherein R$^7$ is hydrogen, alkyl, aryl, aromatic or aliphatic acyl, or aralkyl, and X and Y each is independently O, S, imino which is unsubstituted or substituted by alkyl or alkoxy, or methylene which is unsubstituted or substituted by alkyl, alkoxy, hydroxy or halogen.

2. The compound claimed in claim 1, wherein X and Y each is independently methylene which is unsubstituted or substituted by alkyl, alkoxy, hydroxy or halogen.

3. The compound claimed in claim 1, wherein X is O and Y is methylene which is unsubstituted or substituted by alkyl, alkoxy, hydroxy or halogen.

4. The compound claimed in claim 1, wherein X is S and Y is methylene which is unsubstituted or substituted by alkyl, alkoxy, hydroxy or halogen.

5. The compound claimed in claim 1, wherein X is methylene which is unsubstituted or substituted by alkyl, alkoxy, hydroxy or halogen and Y is O or S.

6. The compound claimed in claim 1, 2, 3, 4, or 5 wherein R$^5$ is hydrogen and R$^6$ is alkyl, hydroxy, alkoxy, or acetoxy.

7. The compound claimed in claim 1, 2, 3, 4, or 5 wherein R$^5$ is alkyl, R$^6$ is alkyl, hydroxy, alkoxy, or acetoxy.

8. The compound claimed in claim 1, 2, 3, 4, or 5 wherein R$^5$ is hydrogen, R$^6$ is amino which is substituted by alkyl, hydroxy, alkoxy, aromatic or aliphatic acyl, or alkoxycarbonyl.

9. The compound claimed in claim 6, wherein R$^1$ and R$^2$ each is tert-butyl at the same time.

10. The compound claimed in claim 7, wherein R$^1$ and R$^2$ each is tert-butyl at the same time.

11. The compound claimed in claim 8, wherein R$^1$ and R$^2$ each is tert-butyl at the same time.

* * * * *

UNITED STATES PATENT AND TRADEMARK OFFICE
CERTIFICATE OF CORRECTION

PATENT NO. : 5,319,099

DATED : June 7, 1994

INVENTOR(S) : Susumu KAMATA et al.

It is certified that error appears in the above-indentified patent and that said Letters Patent is hereby corrected as shown below:

Col. 34, line 6-15, Claim 1 replace the formula with the following formula:

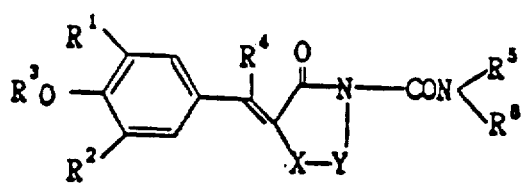

Signed and Sealed this

Second Day of May, 1995

BRUCE LEHMAN

Attest:

Attesting Officer

Commissioner of Patents and Trademarks